United States Patent
Vukelic et al.

(10) Patent No.: US 11,497,403 B2
(45) Date of Patent: Nov. 15, 2022

(54) DEVICES, METHODS, AND SYSTEMS FOR DETECTION OF COLLAGEN TISSUE FEATURES

(71) Applicant: The Trustees of Columbia University in the City of New York, New York, NY (US)

(72) Inventors: Sinisa Vukelic, New York, NY (US); Gerard A. Ateshian, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 969 days.

(21) Appl. No.: 16/308,306

(22) PCT Filed: Jun. 10, 2017

(86) PCT No.: PCT/US2017/036915
§ 371 (c)(1),
(2) Date: Dec. 7, 2018

(87) PCT Pub. No.: WO2017/214604
PCT Pub. Date: Dec. 14, 2017

(65) Prior Publication Data
US 2019/0246907 A1     Aug. 15, 2019

Related U.S. Application Data

(60) Provisional application No. 62/348,502, filed on Jun. 10, 2016.

(51) Int. Cl.
*G01J 3/44*     (2006.01)
*A61B 5/00*     (2006.01)
*G01J 3/02*     (2006.01)

(52) U.S. Cl.
CPC .......... *A61B 5/0075* (2013.01); *A61B 5/4514* (2013.01); *G01J 3/44* (2013.01); *G01J 3/0218* (2013.01); *G01J 3/0229* (2013.01)

(58) Field of Classification Search
CPC ........ A61B 5/0075; A61B 5/4514; G01J 3/44; G01J 3/0218; G01J 3/0229; G01N 21/65
See application file for complete search history.

(56) References Cited

U.S. PATENT DOCUMENTS

| 4,638,801 A | 1/1987 | Daly et al. |
| 4,784,135 A | 11/1988 | Blum et al. |

(Continued)

FOREIGN PATENT DOCUMENTS

| EP | 2283344 A1 | 2/2011 |
| EP | 1742311 B1 | 3/2011 |

(Continued)

OTHER PUBLICATIONS

Caporossi et al., "Long-term Results of Riboflavin Ultraviolet A Corneal Collagen Cross-linking for Keratoconus in Italy: The Siena Eye Cross Study" Am J Ophthalmol. Apr. 2010; 149(4): pp. 585-593.

(Continued)

*Primary Examiner* — Abdullahi Nur
(74) *Attorney, Agent, or Firm* — Potomac Law Group, PLLC

(57) ABSTRACT

The present application discloses methods, devices, and systems for generating spatially-resolved quantification of cross-linking in cartilage based on Raman scattering of excitation light. The examples presented demonstrate that the method provides a discriminating power sufficient to distinguish early onset of osteo-arthritis even before a patient is symptomatic.

22 Claims, 18 Drawing Sheets

(56) References Cited

U.S. PATENT DOCUMENTS

| | | | |
|---|---|---|---|
| 4,840,175 A | 6/1989 | Peyman | |
| 5,334,190 A | 8/1994 | Seiler | |
| 5,556,406 A | 9/1996 | Gordon et al. | |
| 5,720,894 A | 2/1998 | Neev et al. | |
| 5,735,843 A | 4/1998 | Trokel | |
| 5,861,955 A | 1/1999 | Gordon | |
| 6,099,521 A | 8/2000 | Shadduck | |
| 6,110,166 A | 8/2000 | Juhasz | |
| 6,146,375 A | 11/2000 | Juhasz et al. | |
| 6,511,800 B1 | 1/2003 | Singh | |
| 6,648,877 B1 | 11/2003 | Juhasz et al. | |
| 6,902,561 B2 | 6/2005 | Kurtz et al. | |
| 6,934,576 B2 | 8/2005 | Camacho et al. | |
| 7,241,461 B2 | 7/2007 | Myhill et al. | |
| 7,413,781 B2 | 8/2008 | Hubbell et al. | |
| 7,645,449 B2 | 1/2010 | Stassi et al. | |
| 7,729,749 B2 | 6/2010 | Roessler et al. | |
| 8,088,124 B2 | 1/2012 | Loesel et al. | |
| 8,114,067 B1 | 2/2012 | Ketteridge et al. | |
| 8,215,314 B2 | 7/2012 | Chan et al. | |
| 8,262,646 B2 | 9/2012 | Frey et al. | |
| 8,279,901 B2 | 10/2012 | Karavitis | |
| 8,343,142 B2 | 1/2013 | König et al. | |
| 8,366,689 B2 | 2/2013 | Marshall et al. | |
| 8,409,177 B1 | 4/2013 | Lai | |
| 8,523,846 B2 | 9/2013 | Makino | |
| 8,528,566 B2 | 9/2013 | Loesel et al. | |
| 8,536,207 B2 | 9/2013 | Yoshida et al. | |
| 8,569,367 B2 | 10/2013 | Vehige et al. | |
| 8,585,686 B2 | 11/2013 | Bergt et al. | |
| 8,617,147 B2 | 12/2013 | Knox et al. | |
| 8,688,199 B2 | 4/2014 | Dudhia et al. | |
| 8,784,406 B2 | 7/2014 | Rathjen | |
| 8,915,905 B2 | 12/2014 | Vogler et al. | |
| 8,974,444 B2 | 3/2015 | Alfano et al. | |
| 9,095,414 B2 | 8/2015 | Jester et al. | |
| 9,101,446 B2 | 8/2015 | Bor et al. | |
| 9,125,599 B2 | 9/2015 | Chen | |
| 9,125,856 B1 | 9/2015 | Paik et al. | |
| 9,155,652 B2 | 10/2015 | Peyman | |
| 9,226,853 B2 | 1/2016 | Bor et al. | |
| 9,271,870 B2 | 3/2016 | Palanker et al. | |
| 9,504,607 B2 | 11/2016 | Russmann | |
| 9,539,143 B2 | 1/2017 | Holliday et al. | |
| 9,545,340 B1 | 1/2017 | Knox et al. | |
| 9,555,111 B2 | 1/2017 | Rubinfeld et al. | |
| 9,622,911 B2 | 4/2017 | Rubinfeld et al. | |
| 9,622,912 B2 | 4/2017 | Knox et al. | |
| 9,681,984 B2 | 6/2017 | Peyman | |
| 9,695,218 B2 | 7/2017 | Yang et al. | |
| 9,814,567 B2 | 11/2017 | Peyman | |
| 9,883,970 B2 | 2/2018 | Lopath et al. | |
| 10,448,819 B2 | 10/2019 | Weeber | |
| 2005/0119587 A1 | 6/2005 | Roessler et al. | |
| 2005/0129685 A1 | 6/2005 | Cao et al. | |
| 2007/0049808 A1 | 3/2007 | Roessler et al. | |
| 2007/0213792 A1 | 9/2007 | Yaroslavsky et al. | |
| 2008/0031923 A1 | 2/2008 | Murray et al. | |
| 2008/0094572 A1 | 4/2008 | Lai | |
| 2009/0024117 A1 | 1/2009 | Muller | |
| 2009/0171325 A1 | 7/2009 | Koenig | |
| 2009/0171327 A1 | 7/2009 | Kurtz et al. | |
| 2010/0004643 A1 | 1/2010 | Frey et al. | |
| 2010/0027282 A1 | 2/2010 | Gebauer et al. | |
| 2010/0210996 A1 | 8/2010 | Peyman | |
| 2010/0216226 A1 | 8/2010 | Hyde et al. | |
| 2010/0272824 A1 | 10/2010 | Lupton et al. | |
| 2010/0286156 A1 | 11/2010 | Pinelli | |
| 2010/0318017 A1 | 12/2010 | Lewis et al. | |
| 2011/0077624 A1 | 3/2011 | Brady et al. | |
| 2011/0208300 A1 | 8/2011 | de Juan et al. | |
| 2012/0083772 A1 | 4/2012 | Rubinfeld et al. | |
| 2012/0083776 A1 | 4/2012 | Dai et al. | |
| 2012/0310223 A1 | 12/2012 | Knox et al. | |
| 2012/0330291 A1 | 12/2012 | Jester et al. | |
| 2013/0116757 A1 | 5/2013 | Russmann | |
| 2013/0245536 A1 | 9/2013 | Friedman et al. | |
| 2013/0245617 A1 | 9/2013 | Rathjen | |
| 2013/0267528 A1 | 10/2013 | Pinelli | |
| 2013/0338650 A1 | 12/2013 | Jester et al. | |
| 2014/0066835 A1 | 3/2014 | Muller et al. | |
| 2014/0140594 A1* | 5/2014 | Mahadevan-Jansen ..................... G06T 7/0012 382/128 |
| 2014/0155871 A1 | 6/2014 | Cumming | |
| 2014/0155872 A1 | 6/2014 | Stevens | |
| 2014/0171927 A1 | 6/2014 | Depfenhart | |
| 2015/0032091 A1 | 1/2015 | Teuma et al. | |
| 2015/0126921 A1 | 5/2015 | Rubinfeld et al. | |
| 2015/0133901 A1 | 5/2015 | Serdarevic et al. | |
| 2015/0144792 A1 | 5/2015 | Gunn | |
| 2015/0305933 A1 | 10/2015 | Zhou | |
| 2015/0359668 A1 | 12/2015 | Kornfield et al. | |
| 2016/0059032 A1 | 3/2016 | Skerl | |
| 2016/0101045 A1 | 4/2016 | Raymond et al. | |
| 2016/0106590 A1 | 4/2016 | Bischoff et al. | |
| 2016/0136109 A1 | 5/2016 | Isenburg et al. | |
| 2016/0151202 A1 | 6/2016 | Scarcelli et al. | |
| 2016/0310319 A1 | 10/2016 | Friedman et al. | |
| 2016/0338588 A1 | 11/2016 | Friedman | |
| 2016/0374857 A1 | 12/2016 | Fu et al. | |
| 2016/0374858 A1 | 12/2016 | Goos et al. | |
| 2017/0021021 A1 | 1/2017 | Kamaev et al. | |
| 2017/0043015 A1 | 2/2017 | Alageel et al. | |
| 2017/0246471 A1 | 8/2017 | Lopath | |
| 2017/0319383 A1 | 11/2017 | Luttrull et al. | |
| 2018/0021086 A1 | 1/2018 | Deladurantaye et al. | |
| 2018/0021172 A1 | 1/2018 | Zheleznyak et al. | |
| 2018/0050104 A1 | 2/2018 | Xie et al. | |
| 2018/0160898 A1 | 6/2018 | Yoo et al. | |
| 2018/0177550 A1 | 6/2018 | Anderson et al. | |
| 2018/0221201 A1 | 8/2018 | Vukelic et al. | |

FOREIGN PATENT DOCUMENTS

| | | |
|---|---|---|
| WO | 1998005279 A1 | 2/1998 |
| WO | 2000074648 A2 | 12/2000 |
| WO | 2006061565 A1 | 6/2006 |
| WO | 2009073600 A1 | 6/2009 |
| WO | 2011046236 A9 | 7/2011 |
| WO | 2012145159 A1 | 10/2012 |
| WO | 2014065863 A1 | 5/2014 |
| WO | 2014159691 A1 | 10/2014 |
| WO | 2014210152 A2 | 12/2014 |
| WO | 2015010119 A2 | 1/2015 |
| WO | 2015138786 A1 | 9/2015 |
| WO | 2015162559 A1 | 10/2015 |
| WO | 2015138794 A9 | 3/2016 |
| WO | 2016100411 A2 | 6/2016 |
| WO | 2017031167 A1 | 2/2017 |
| WO | 2017070637 A1 | 4/2017 |
| WO | 2018119453 A1 | 6/2018 |

OTHER PUBLICATIONS

De Ortueta et al., "High-speed recording of thermal load during laser trans-epithelial corneal refractive surgery using a 750 Hz ablation system," Journal of Optometry, Jul. 20, 2018, vol. 12 (2), pp. 84-91.

Dorronsoro et al., "Dynamic OCT measurement of corneal deformation by an air puff in normal and cross-linked corneas". Biomedical Optics Express, vol. 3 / Issue 3, pp. 473-487, Feb. 2012.

International Search Report and Written Opinion dated Feb. 5, 2020 for International Patent Application No. PCT/US2019/063320.

Kanellopoulos et al., "Topography-guided Hyperopic LASIK With and Without High Irradiance Collagen Cross-linking: Initial Comparative Clinical Findings in a Contralateral Eye Study of 34 Consecutive Patients", Journal of Refractive Surgery, vol. 28 / Issue 11, pp. S837-S840, Nov. 2012.

Luz et al., "Application of corneal tomography before keratorefractive procedure for laser vision correction", Journal of Biophotonics, vol. 9 / Issue 5, pp. 445-453, Apr. 2016.

(56) References Cited

OTHER PUBLICATIONS

Meek et al., "Corneal cross-linking—a review", Ophthal Physiol Optics. Feb. 2013; 33(2): pp. 78-93.
Pedrigi et al., "Regional mechanical properties and stress analysis of the human anterior lens capsule", Vision Research, vol. 47 / Issue 13, pp. 1781-1789, Jun. 2007.
Rossi et al., "Modeling the load resistance in laser-assisted cornea transplantation", Proceedings of SPIE: Ophthalmic Technologies, vol. 10858, Feb. 2019.
Zaitsev et al., "Optical coherence elastography for strain dynamics measurements in laser correction of cornea shape", Journal of Biophotonics, vol. 10 / Issue 11, pp. 1450-1463, 2017.
International Search Report and Written Opinion dated Jun. 11, 2019 for International Patent Application No. PCT/US2019/024321.
Turunen at al; "Pico- and femtosecond laser-induced crosslinking of protein microstructures: evaluation of processability and bioactivity"; Biofabrication 3 (2011) 045002 (14pp).
Vaddavalli et al., "Air bubble in anterior chamber as indicator of full-thickness incisions in femtosecond-assisted astigmatic keratotomy," Journal of Cataract & Refractive Surgery, Sep. 1, 2011, vol. 37(9), pp. 1723-1725.
Vazirani et al., "Keratoconus: current perspectives," Clinical Ophthalmology, vol. 7, pp. 2019-2030, Oct. 2013.
Vinciguerra P, et al. "Corneal collagen crosslinking for ectasia after excimer laser refractive surgery: 1-year results." J Refract Surg. 2010;26:486-497.
Vukelic et al., "Investigation of the morphology of the features generated via femtosecond lasers in the interior of a bovine cornea sections", SPIE Proceedings vol. 8579, Optical Interactions with Tissue and Cells XXIV, 857904, Feb. 15, 2013. 10 pages.
Vukelic et al.; "Ultrafast Laser Induced Structural Modification of Fused Silica—Part II: Spatially Resolved and Decomposed Raman Spectral Analysis"; Journal of Manufacturing Science and Engineering; 132; No. 6:061013; 2010.
Wang C, et al. "Quantitative analysis of Raman spectra for assessment of cross link concentrations toward diagnosing early osteoarthritis." Summer Biomechanics, Bioengineering and Biotransport Conference. Snowbird UT, USA (2015).
Wang C., et al. "Femtosecond Laser Irradiation as Novel Paradigm for Treatment of Early Osteoarthritis," Annual Meeting of the Orthopaedic Research Society. San Diego, CA, USA (2017).
Wang et al.;"A New Paradigm for Use of Ultrafast Lasers in Ophthalmology for Enhancement of Corneal Mechanical Properties and Permanent Correction of Refractive Errors"; Proc. of SPIE vol. 10066; Energy-based Treatment of Tissue and Assessment IX, 100660Y. Feb. 2017.
Wang, C., et al. "Near-infrared Femtosecond Laser as a potential Tool for non-invasive Refractive Error Corrections," In preparation (2017).
Wang, C., et al. "Quantitative Raman characterization of cross-linked collagen thin films as a model system for diagnosing early osteoarthritis," SPIE BiOS, International Society for Optics and Photonics, 970415-970415 (2016).
Wei et al., "Comparison of corneal sensitivity between FS-LASIK and femtosecond lenticule extraction (ReLEx flex) or small-incision lenticule extraction (ReLEx smile) for myopic eyes," Graefes Archive for Clinical and Experimental Ophthalmology, Feb. 7, 2013, vol. 251(6), pp. 1645-1654.
Wei et al., "Erratum to: Comparison of corneal sensitivity between FS-LASIK and femtosecond lenticule extraction (ReLEx flex) or small-incision lenticule extraction (ReLEx smile) for myopic eyes," Graefes Archive for Clinical and Experimental Ophthalmology, May 1, 2013, vol. 251, pp. 2495-2497.
West et al.; "Fourier Transform Infrared Spectral Analysis of Degenerative Cartilage: An Infrared Fiber Optic Probe and Imaging Study"; Applied Spectroscopy; 58(4); pp. 376-381; 2004.
Wilkinson et al.; "Refractive eye surgery: helping patients make informed decisions about LASI"; Am Fam Physician. May 15, 2017: 95(10): pp. 637-644.

Wilson SE, et al "Epithelial injury induces keratocyte apoptosis: hypothesized role for theinterleukin-1 system in the modulation of corneal tissue organization and wound healing." Exp Eye Res. Apr. 1996; 62 (4): 325-7.
Wilson SE, et al "Herpes simplex virus type-1 infection of corneal epithelial cells induces apoptosis of die underlying keratocytes " Exp Eye Res. 1997;64:775-779.
Wise et al "Cytokine Expression in Keratoconus and its Corneal Microenvironment"—A Systematic Review, 2015.
Wollensak et al., "Riboflavin/ultraviolet-A-induced collagen crosslinking for the treatment of keratoconus"; Am J Ophthalmol 2003;135:620-627.
Wollensak et al., "Biomechanical Efficacy of Collagen Crosslinking in Porcine Cornea Using a Femtosecond Laser Pocket", Cornea (Mar. 1, 2014) vol. 33(3), pp. 300-305.
Wollensak G, et al. "Hydration behavior of porcine cornea crosslinked with riboflavin and ultraviolet A."; J Cataract Refract Surg. 2007;33:516-521.
Wollensak G,et al. "Interlamellar cohesion after corneal collagen crosslinking using riboflavin and ultraviolet A light.";Br J Ophthalmol. 2011;95:876-880.
Wollensak G. "Corneal collagen crosslinking: new horizons."; Expert Rev Ophthalmol. 2010;5:201-215.
Wollensak, G. et al. "Biomechanical and histological changes after corneal crosslinking with and without epithelial debridement," Journal of Cataract & Refractive Surgery, 35(3), 540-546 (2009).
Wollensak, G. et al. "Long-term biomechanical properties of rabbit cornea after photodynamic collagen crosslinking," Acta ophthalmologica, 87(1), 48-51 (2009).
Wollensak, G., "Crosslinking treatment of progressive keratoconus: new hope," Current opinion in ophthalmology, 17(4), 356-360 (2006).
Xia et al., "Low-intensity pulsed ultrasound treatment at an early osteoarthritis stage protects rabbit cartilage from damage via the integrin/focal adhesion kinase/mitogen-activated protein kinase signaling pathway," Journal of Ultrasound in Medicine, Nov. 1, 2015, vol. 34(11), pp. 1991-1999.
Xia et al.; The depth-dependent anisotropy of articular cartilage by Fourier transform infrared imaging (FTIRI); Osteoarthritis and Cartillage 15; pp. 780-788; 2007.
Zhao et al.; "Automated Autofluorescence Background Subtraction Algorithm for Biomedical Raman Spectroscopy"; Applied Spectroscopy; First Published Nov. 1, 2007; vol. 6II Issue 11; pp. 1225-1232.
Zipfel, W.R., et al. "Live tissue intrinsic emission microscopy using multiphoton-excited native fluorescence and second harmonic generation," Proceedings of the National Academy of Sciences, 100(12), 7075-7080 (2003).
Clinical Trial No. NCT02208089, "Simultaneous TransPRK and Corneal Collagen Cross-Linking (TransPRKCXL)", Sponsor: Bruce Allan, Moorfields Eye Hospital NHS Foundation Trust, Aug. 4, 2014.
International Search Report and Written Opinion issued in International Application No. PCT/US2019/040728 dated Sep. 18, 2019.
International Preliminary Report on Patentability dated Aug. 6, 2020, issued in International Application No. PCT/US2019/015095.
International Preliminary Report on Patentability dated Oct. 8, 2020, issued in International Application No. PCT/US2019/024321.
Deberg et al., "New serum biochemical markers (Coll 2-1 and Coll 2-1 NO2) for studying oxidative related type II collagen network degradation in patients with osteoarthritis and rheumatoid arthritis", Osteoarthritis and Cartilage, Mar. 2005, 13 (3), pp. 258-265.
Dijkgraaf et al., "Normal cartilage structure, biochemistry, and metabolism: A review of the literature" J Oral Maxillofac Surg. Oct. 1995; 53(10): pp. 924-929.
Dijkgraaf et al., "The structure, biochemistry, and metabolism of osteoarthritic cartilage: A review of the literature", J Oral Maxillofac Surg. Oct. 1995; 53(10): pp. 1182-1192.
S. Turunen et al., "Pico- and femtosecond laser-induced crosslinking of protein microstructures: evaluation ofprocessability and bioactivity", 2011 Biofabrication 3 045002 (http://iopscience.iop.org/1758-5090/3/4/045002), downloaded Oct. 9, 2011, pp. 1-14.

(56) References Cited

OTHER PUBLICATIONS

Saarakkala et al., "Specificity of Fourier Transform Infrared (FUR) microspectroscopy to estimate depth wise proteoglycan content in normal and osteoarthritic human articular cartilage" Cartilage, Oct. 2010, 1 (4), pp. 262-269.

Vogel et al., "Low-Density Plasma Below the Optical Breakdown Threshold—Potential Hazard for Multiphoton Microscopy, and a Tool for the Manipulation of Intracellular Events", Proc. SPIE vol. 4620, Multiphoton Microscopy in the Biomedical Sciences II, 2002, 15 pages.

Aristeidou et al., "The evolution of corneal and refractive surgery with the femtosecond laser", Eye Vis (Lond), Jul. 14, 2015, vol. 2(12), pp. epub.

Ashkavand et al., "The pathophysiology of osteoarthritis", Journal of Pharmacy Research, vol. 7(1), pp. 132-138, 2013.

Bakilan et al., "Effects of Native Type II Collagen Treatment on Knee Osteoarthritis: A Randomized Controlled Trial", Eurasian Journal of Medicine, vol. 48(2), pp. 95-101, Jun. 2016.

Bekesi et al., "Biomechanical Changes After In Vivo Collagen Cross-Linking With Rose Bengal-Green Light and Riboflavin-UVA", Invest Ophthalmol Vis Sci, Mar. 1, 2017, vol. 58(3), pp. 1612-1620.

Bradford et al., "Custom built nonlinear optical crosslinking (NLO CXL) device capable of producing mechanical stiffening in ex vivo rabbit corneas", Biomedical Optics Express, vol. 8(10), pp. 4788-4797, Sep. 2017.

Collier et al., "Estimated burden of Keratitis—United States, 2010", MMWR Morb Mortal Wkly Rep, vol. 63(45), pp. 1027-1030, Nov. 14, 2014.

De Macedo et al., "Femtosecond laser-assisted deep anterior lamellar keratoplasty in phototherapeutic keratectomy versus the big-bubble technique in keratoconus", International Journal Ophthalmology, vol. 11(5), pp. 807-812, May 2018.

De Medeiros et al., "Effect of femtosecond laser energy level on corneal stromal cell death and inflammation", Journal of Refractive Surgery, vol. 25(10), pp. 869-874, Apr. 2009.

Deibel et al., "Ocular inflammation and infection", Emerg Med Clin North A, May 2013, vol. 21(2), pp. 387-397.

Dolgin, "Parkinson's drug makers target inflammasome", Nature Biotechnology, Jan. 2019.

Eyre, "Collagen cross-linking in skeletal aging and disease", NIH Grant# 5R37AR037318-32, Awardee: University of Washington.

Gallego-Munoz et al., "Corneal Wound Repair After Rose Bengal and Green Light Crosslinking: Clinical and Histologic Study", Invest Ophthalmol Vis Sci, Jul. 1, 2017, vol. 58(9), pp. 3471-3480.

Gutierrez-Bonnet et al., "Macular Choroidal Thickening in Keratoconus Patient: Swept-Source Optical Coherence Tomography Study", Translational Vision Science & Technology, vol. 7(3), p. 15, Jun. 2018.

International Preliminary Report on Patentability issued in International Application No. PCT/US2017/036915 dated Dec. 20, 2018.

International Search Report and Written Opinion for International Application No. PCT/US2019/015095 dated Apr. 22, 2019.

Jester et al., "Non-Linear Optical Collagen Cross-Linking (NLO CXL) for Treatment of Keratoconus", Project No. 5R01EY024600-04, Jul. 31, 2019.

Jones et al., "Nanoscale dysregulation of collagen structure-function disrupts mechano-homeostasis and mediates pulmonary fibrosis", eLife, vol. 7, pii: e36354, Jul. 2018.

Kempen et al., "The prevalence of refractive errors among adults in the United States, Western Europe, and Australia", Arch Ophthalmol., Apr. 2004, vol. 122(4), pp. 495-505.

Kymionis et al., "Simultaneous topography-guided PRK followed by corneal collagen cross-linking for keratoconus", Journal of Refractory Surgery, vol. 25(9), pp. S807-S822, Sep. 2009.

Legrand et al., "Glycation Marker Glucosepane Increases with the Progression of Osteoarthritis and correlates with Morphological and Functional changes of Cartilage in vivo", Arthritis Research & Therapy, vol. 20(1), p. 131, Jun. 2018.

Mittal et al., "Reactive oxygen species in inflammation and tissue injury", Antoxid Redox Signal, Oct. 2013, vol. 20(7), pp. 1126-1167.

Patel et al., "Keratocyte progenitor cell transplantation: A novel therapeutic strategy for corneal disease", Medical Hypotheses, vol. 80(2), pp. 122-124, Feb. 2013.

Price et al., "Photoactivated riboflavin treatment of infectious keratitis using collagen cross-linking technology", Journal of Refractive Surgery, vol. 28(10), pp. 706-713, Oct. 2012.

Rapuano et al., "Antimicrobial Studies Using the Therapeutic Tissue Cross-Linking Agent, Sodium Hydroxymethylglycinate: Implication for Treating Infectious Keratitis", IOVS, vol. 59(1), pp. 332-337, Jan. 2018.

Sakimoto et al., "Laser eye surgery for refractive errors", The Lancet, Apr. 29, 2006, vol. 367(9520), pp. 1432-1447.

Sharif et al., "Human in vitro Model Reveals the Effects of Collagen Cross-linking on Keratoconus Pathogenesis", Scientific Reports, vol. 7(1), Oct. 2017.

Shetty et al., "Collagen crosslinking in the management of advanced non-resolving microbial keratitis", Br J Opthalmol, Aug. 2014, vol. 98(8), pp. 1033-1055.

Song et al., "Viability, apoptosis, proliferation, activation, and cytokine secretion of human keratoconus keratocytes after cross-linking", Biomedical Research International, Epub 2015:253237, Jan. 2015.

Stantchev et al., "Subwavelength hyperspectral THz Studies of Articular Cartilage", Scientific Reports, vol. 8, Published online May 2, 2018.

Tabibian et al., "PACK-CXL: Corneal Cross-linking for Treatment of Infectious Keratitis", Journal of Ophthalmic & Vision Research, vol. 10(1), pp. 77-80, Jan. 2015.

Unknown, "New Method Could Offer More Precise Treatment for Corneal Disease", The Optical Society, May 4, 2016.

Unknown, "New noninvasive reflective treatment on the horizon", EyeWorld, Oct. 2018.

Wang et al., "Femtosecond laser crosslinking of the cornea for non-invasive vision correction", Nature Photonics, vol. 12, pp. 416-422, May 2018.

Xie et al., "Robust increase of cutaneous sensitivity, cytokine production and sympathetic sprouting in rats with localized inflammatory irritation of the spinal ganglia", Neuroscience, Nov. 2006, vol. 142(3), pp. 809-822.

Zayed et al., "Xenogenic Implantation of Equine Synovial Fluid-Derived Mesenchymal Stem Cells Leads to Articular Cartilage Regeneration", Stem Cells Int, Jun. 2018.

Zhang et al., "Cytokines, inflammation and pain", Int Anesthesiol Clin, Nov. 2009, vol. 45(2), pp. 27-37.

Zhu et al., "Corneal Crosslinking With Rose Bengal and Green Light: Efficacy and Safety Evaluation", Cornea,. Sep. 2016, vol. 35(9), pp. 1234-1241.

Kanellopoulos, A.J. et al. "Collagen cross-linking (CCL) with sequential topography-guided PRK: a temporizing alternative for keratoconus to penetrating keratoplasty" Cornea, 26(7), 891-895 (2007).

Karamburoglu, G., et al "Intacs implantation with sequential collagen cross-linking treatment in postoperative LASIK ectasia."; J Refract Surg 2008;24:S726-S729.

Kato et al., "Topography-Guided Conductive Keratoplasty: Treatment for Advanced Keratoconus", American Journal of Ophthalmology, Oct. 1, 2010, vol. 150(4), pp. 481-489.

Kermani O, et al. "Comparative micromorphologic in vitro porcine study of IntraLase and femto LDV femtosecond lasers."; J Cataract Refract Surg. 2008;34:1393-1399.

Kilic, A, et al "Riboflavin injection into the corneal channel for combined collagen crosslinking and intrastromal corneal ring segment implantation."; J Cataract Retract Surg. 2012:38:878-883.

Kling S, et al "Corneal biomechanical changes after collagen cross-linking from porcine eye inflation experiments" IOVS vol. 51/Issue 8, pp. 3961-3968, Aug. 2010.

Kolli, S. "Safety and efficacy of collagen crosslinking for the treatment of keratoconus" Expert opinion on drug safety, 9(6), 949-957 (2010).

(56) References Cited

OTHER PUBLICATIONS

Konig et al., "Intratissue surgery with 80 MHz nanojoule femtosecond laser pulses in the near infrared," Optics Express, Feb. 11, 2002, vol. 10(3), pp. 171-176.
Krueger RR, et al "Staged intrastromal delivery of riboflavin with UVA cross-linking in advanced bullous keratopathy: laboratory investigation and first clinical case." J Refract Surg. 2008;24:S730-S736.
Kwok et al., "Selective two-photon collagen crosslinking in situ measured by Brillouin microscopy," Optica, May 20, 2016, vol. 3(5), pp. 469-472.
Leccisotti A, et al "Transepithelial corneal collagen cross-linking in keratoconus." J Refract Surg. 2010;26:942-948.
Leger et al.;"Comparison of Derivative Preprocessing and Automated Polynomial Baseline Correction Method for Classification and Quantification of Narcotics in Solid Mixtures"; Society for Applied Spectroscopy; vol. 60; No. 2; pp. 182-193; 2006.
Letnikova et al., "Femtosecond Corneal Collagen Crosslinking in Treatment of Patients with Progressive Keratoconus Stages I-II," Clinical and Translational Medicine, 2016 (full date not available), vol. 8(1), pp. 128-132.
Lim et al.; "Epithelium-on photorefractive intrastromal cross-linking (PiXL) for reduction of low myopia"; Clin Ophthalmol. 2017; 11: pp. 1205-1211.
Liu et al. "Corneal Epithelial Wound Healing"; Progress in Molecular Biology and Translational Science, Academic Press, vol. 134, 2015, pp. 61-71.
Lombardo M, et al. "Biomechanics of the anterior human corneal tissue investigated with atomic force microscopy."; Invest Ophthalmol Vis Sci. 2012;53:1050-1057.
Lubatschowski, H., et al "Application of ultrashort laser pulses for intrastromal refractive surgery," Graefe's archive for clinical and experimental ophthalmology, 238(1), 33-39 (2000).
Marshall, J., et al. "Long-term healing of the central cornea after photorefractive keratectomy using an excimer laser," Ophthalmology, 95(10), 1411-1421 (1988).
Matheson, I.B.C., et al "The quenching of singlet oxygen by amino acids and proteins," Photochemistry and photobiology, 21(3), 165-171 (1975).
Mayo et al.; "Course notes on the interpretation of infrared and Raman spectra"; John Wiley & Sons, Inc.; 2003.
Mazet et al.; "Background removal from spectra by designing and minimising a non-quadratic cost function"; Chemometrics and Intelligent Laboratory Systems 76 (2005) pp. 121-133.
Medeiros FW, et al. "Biomechanical corneal changes induced by different flap thickness created by femtosecond laser."; Clinics (Sao Paulo). 2011;66:1067-1071.
Meier;"On art and science in curve-fitting vibrational spectra"; Vibrational Spectroscopy; vol. 39; Issue 2; pp. 266-269; Mar. 10, 2005.
Meltendorf et al., "Corneal intrastromal tissue modeling with the femtosecond laser," Graefes Archive for Clinical and Experimental Ophthalmology, Nov. 1, 2011, vol. 249(11), pp. 1661-1666.
Migneault et al.; "Glutaraldehyde: behavior in aqueous solution, reaction with proteins, and application to enzyme crosslinking"; BioTechniques 37:790-802; Nov. 2004.
Munnerlyn, C.R., et al "Photorefractive keratectomy: a technique for laser refractive surgery," Journal of Cataract & Refractive Surgery, 14(1), 46-52 (1988).
Nan Shen, "Photodisruption in biological tissues using femtosecond laser pulses." Diss. Harvard University Cambridge,Massachusetts, (2003).
Naoyuki Morishige et al. "Quantitative Analysis of Collagen Lamellae in the Normal and Keratoconic Human Cornea by Second Harmonic Generation Imaging Microscopy," Investigative Ophthalmology & Visual Science Dec. 2014, vol. 55, 8377-8385.
Netto MV, Mohan RR, Ambrosio R Jr, Hutcheon AEK, Zieske JD, Wilson SE. Wound healing in the cornea: a review of refractive surgery complications and new prospects for therapy. Cornea Jul. 2005; 24(5): pp. 509-522.
Nguyen et al., "Corneal collagen cross-linking in the stabilization of PRK, LASIK, thermal keratoplasty, and orthokeratology," Current Opinion in Ophthalmology, Jul. 1, 2013, vol. 24(4), pp. 291-295.
Nover AB, et al "Longterm storage and preservation of tissue engineered articular cartilage." J Orthop Res. Jan. 2016; 34(1):141-8.
Park, C.Y. et al "Second Harmonic Generation Imaging Analysis of Collagen Arrangement in Human Cornea" Investigative ophthalmology & visual science, 56(9), 5622-5629 (2015).
Poli M, et al. "Prospective study of corneal collagen cross-linking efficacy and tolerance in the treatment of keratoconus and corneal ectasia: 3-year results" Cornea. 2013;32:583-590.
Rabinowitz, "Keratoconus," Survey of Ophthalmology, Jan.-Feb. 1998, vol. 42(4), pp. 297-319.
Raiskup-Wolf et al., "Collagen crosslinking with riboflavin and ultraviolet—A light in keratoconus: Long-term results", Journal of Cataract & Refractive Surgery, vol. 34 (5), May 1, 2008, pp. 796-801.
Reddy et al., "Laser photostimulation of collagen production in healing rabbit achilles tendons," Lasers in Surgery and Medicine, Jan. 1, 1998, vol. 22(5), pp. 281-287.
Ricard-Blum et al.; "Collagen Cross-Linking"; Int. J. Biochem, vol. 21, No. 11, pp. 1185-1189; Apr. 27, 1989.
Rich et al.; "The Molecular Structure of Collagen"; J. Mol. Biol. (1961) 3; pp. 483-506; Feb. 23, 1961.
Rocha et al., "Comparative study of riboflavin-UVA cross-linking and "flash-linking" using surface wave elastometry," Journal of Refractive Surgery, Sep. 1, 2008, vol. 24(7), pp. S748-S751.
Romero-Jimenez, M., et al. "Keratoconus: a review. Contact Lens and Anterior Eye," 33(4), 157-166 (2010).
Sagoo et al2004; "Inflammatory Cytokines Induce Apoptosis of Corneal Endothelium through Nitric Oxide"; Investigative Ophthalmology & Visual Science Nov. 2004, vol. 45, 3964-3973. doi:10.1167/iovs.04-0439.
Salomão MQ1, et al "Corneal wound healing after ultraviolet-A/riboflavin collagen cross-linking: a rabbit study" J Refract Surg. Jun. 2011;27(6):401-7. doi: 10.3928/1081597X-20101201-02. Epub Dec. 1, 2010.
Schumacher S, et al "Absorption of UV-light by riboflavin solutions with different concentration."; J Refract Surg. 2012;28:91-92.
Sidhu et al., "Femtosecond laser-assisted selective reduction of neovascularization in rat cornea," Lasers in Medical Science, Jul. 1, 2014, vol. 29(4), pp. 1417-1427.
Singh, A., et al. "Possible formation of singlet oxygen from vibrationally excited water," Journal of Photochemistry, 25(2), 99-104 (1984).
Søndergaard AP, et al. "Corneal distribution of riboflavin prior to collagen cross-linking"; Current Eye Research. 2010;35:116-121.
Sorkin et al., "Corneal Collagen Crosslinking: A Systematic Review," Ophthalmologica, vol. 232, pp. 10-27, Apr. 2014.
Spoerl et al., "Corneal Cross-Linking and Safety Issues," The Open Ophthalmology Journal, vol. 5, pp. 14-16, Feb. 2011.
Spoerl, E., et al "Thermomechanical behavior of collagen-cross-linked porcine cornea," Ophthalmologica, 218(2), 136-140 (2004).
Takahashi, Y., et al. "Raman spectroscopy investigation of load-assisted microstructural alterations in human knee cartilage: Preliminary study into diagnostic potential for osteoarthritis" Journal of the Mechanical Behavior of Biomedical Materials vol. 31pp. 77-86Mar. 4, 2014.
Nikogosyan et al., "Two-Photon Ionization and Dissociation of Liquid Water By Powerful Laser UV Radiation", Chemical Physics 77 (1983) 131-143, pp. 131-143.
Albro et al.; "Synovial Fluid and Physiologic Levels of Cortisol, Insulin, and Glucose in Media Maintain the Homeostasis of Immature Bovine Cartilage Explants over Long Term Culture"; Annual Meeting of the Orthopedic Research Society; New Orleans, LA, USA; 2013.
Alexandrov; "A trust-region framework for managing the use of approximation models in optimization"; Structural Optimization 15, 16-23; Springer-Verlag; 1998.
Alió JL, et al. "Cross-linking in progressive keratoconus using an epithelial debridement or intrastromal pocket technique after previous corneal ring segment implantation." J Refract Surg. 2011;27:737-743.

(56) References Cited

OTHER PUBLICATIONS

Asri, D., et al "Corneal collagen crosslinking in progressive keratoconus: multicenter results from the French National Reference Center for Keratoconus," Journal of Cataract & Refractive Surgery, 37(12), 2137-2143 (2011).

Bi; "A novel method for determination of collage orientation in cartilage by Fourier transform infrared imaging spectroscopy (FT-IRIS)", Osteoarthritis and Cartilage 13; p. 1050-1058; 2005.

Bikbova G, et al "Transepithelial corneal collagen cross-linking by iontophoresis of riboflavin." Acta Ophthalmol. 2013 [Epub ahead of print].

Caporossi A, et al. "Riboflavin-UVA-induced corneal collagen cross-linking in pediatric patients." Cornea. 2012;31:227-231.

Chai et al., "Quantitative assessment of UVA-riboflavin corneal cross-linking using nonlinear optical microscopy," Investigative Ophthalmology & Visual Science, Jun. 1, 2011, vol. 52(7), pp. 4231-4238.

Chai, D., et al. "Nonlinear optical collagen cross-linking and mechanical stiffening: a possible photodynamic therapeutic approach to treating corneal ectasia," Journal of biomedical optics, 18(3), 038003-038003 (2013).

Chan et al., "Photochemical crosslinking improves the physicochemical properties of collagen scaffolds," Journal of Biomedical Materials Research Part A, Aug. 16, 2005, vol. 75(3), pp. 689-701.

Charles A. Dinarello, "Interleukin-1", Cytokine & Growth Factor Reviews vol. 8. No. 4, pp. 253-265, 1997.

Chen MC, et al. "Corneal biomechanical measurements before and after laser in situ keratomileusis." J Cataract Refract Surg. 2008;34:1886-1891.

Chen, S., et al "IntraLase femtosecond laser vs mechanical microkeratomes in LASIK for myopia: a systematic review and meta-analysis," Journal of Refractive Surgery, 28(1), 15-24 (2012).

Cherfan D, Verter EE, Melki S, Gisel IE, Doyle FJ Jr, Scarcelli G, Yun SH, Redmond RW, Kochevar IE. Collagen cross-linking using rose bengal and green light to increase corneal stiffness. Invest Ophthalmol Vis Sci. May 13, 2013;54(5):3426-33.

Chu et al.; "Early diagnosis to enable early treatment of pre-osteoarthritis"; Arthritis Research & Therapy 2012; htt;://arthritis-research.com/content/14/3/212.

Chu et al.; "Early diagnosis to enable early treatment of pre-osteoarthritis"; Arthritis Research & Therapy; Jun. 7, 2012.

Daxer A, et al. "Corneal crosslinking and visual rehabilitation in keratoconus in one session without epithelial debridement: new technique"; Cornea. 2010;29:1176-1179.

Demirok et al., "Corneal sensation after corneal refractive surgery with small incision lenticule extraction," Optometry and Vision Science, Oct. 1, 2013, vol. 90(10), pp. 1040-1047.

Dong Z, et al "Collagen cross-linking with riboflavin in a femtosecond laser-created pocket in rabbit corneas: 6-month results";. Am J Ophthalmol. 2011;152:22-27.e1.

Durrie et al., "Femtosecond laser versus mechanical keratome flaps in wavefront-guided laser in situ keratomileusis: Prospective contralateral eye study", Journal of Cataract & Refractive Surgery, Jan. 1, 2005, vol. 31(1), pp. 120-126.

Esmonde-White, K.A., et al "Raman spectroscopy of synovial fluid as a tool for diagnosing osteoarthritis" Journal of Biomedical Optics14(3)pp. 034013 May 14, 2009.

Evans, D.F. et al "Reactivity of the $(1\Delta g)2$ and $1\Delta g$ states of oxygen produced by direct laser excitation," Journal of the Chemical Society, Faraday Transactions 2: Molecular and Chemical Physics, 72, 1661-1666 (1976).

Extended Report and Opinion issued in the corresponding EP Application No. 16858413.4, dated Aug. 30, 2018.

Eydelman M., "Symptoms and satisfaction of patients in the patient-reported outcomes with laser in situ keratomileusis (PROWL) studies", JAMA Ophthalmol. Jan. 1, 2017; 135(1): pp. 13-22.

Eyre et al.; "Cross-linking in collagen and elastin"; Annual Reviews; Biochem.; 53; pp. 717-748; 1984.

Farah, S.G., et al. "Laser in situ keratomileusis: literature review of a developing technique," Journal of Cataract & Refractive Surgery, 24(7), 989-1006 (1998).

Farjadnia M, et al "Corneal cross-linking treatment of keratoconus." Oman.J Ophthalmol vol. 8/ Issue 2 pp. 86-91 May 2015.

Felson et al., "Osteoarthritis: new insights. Part 1: the disease and its risk factors," Annals of Internal Medicine, Oct. 17, 2000, vol. 133(8), pp. 635-646.

Filipello M, et al "Transepithelial corneal collagen crosslinking: bilateral study." J Cataract Refract Surg. 2012;38:283-291.

Friedman et al, "Advanced corneal cross-linking system with fluorescence dosimetry"; Journal of Ophthalmology vol. 2012 Article No. 303459 Jul. 2012.

Gil et al., "Improved self-healing properties of collagen using polyurethane microcapsules containing reactive diisocyanate," Polymer International, Apr. 29, 2016, vol. 65(6), pp. 721-727.

Guo et al., "Femtosecond laser collagen cross-linking without traditional photosensitizers," Optical Interactions with Tissue and Cells XXVI, Mar. 5, 2015, vol. 9321, pp. 932103-1-932103-13.

Guo et al., "Investigation of the formation mechanism and morphology of the features created in the interior of cornea by femtosecond laser pulses," Optical Interactions with Tissue and Cells XXVI, Mar. 1, 2015, vol. 9321, pp. 932106-1-932106-14.

Hardy et al.; "The nature of the cross-linking of proteins by glutaraldehyde. Part 2. The formation of quaternary pyridinium compounds by the action of glutaraldehyde on proteins and the identification of a 3-(2-piperidyl)-pyridinium derivative, anabilysine, as a cross-linking entity"; Journal of the Chemical Soceity; Perkin Transactions; 1:2282-8; 1979.

He, L., et al "Femtosecond laser-assisted cataract surgery," Current opinion in ophthalmology, 22(1), 43-52 (2011).

Helena et al. "Keratocyte apoptosis after corneal surgery," 1997.

Holden et al. "Global prevalence of myopia and high myopia and temporal trends from 2000 through 2050"; Ophthalmology. May 2016;123(5): pp. 1036-1042.

Holzer MP, Rabsilber TM, Auffarth GU. Femtosecond laser-assisted corneal flap cuts: morphology, accuracy, and histopathology. Invest Ophthalmol Vis Sci. Jul. 2006;47(7):2828-31.

Hovakimyan, S., et al "Imaging corneal crosslinking by autofluorescence 2-photon microscopy, second harmonic generation, and fluorescence lifetime measurements." Journal of Cataract & Refractive Surgery, 36(12), 2150-2159 (2010).

Hovhannisyan, V., et al "Photophysical mechanisms of collagen modification by 80 MHz femtosecond laser." Optics express 18, No. 23, 24037-24047 (2010).

International Preliminary Report on Patentability for International Application No. PCT/US2016/058353 dated May 3, 2018.

International Search Report and Written Opinion for International Application No. PCT/US2016/058353 dated Feb. 21, 2017.

J.K.F. Tait et al.; "Fourier transform Raman spectroscopic examination of two amine-based epoxy resin crosslinking agents"; Elsevier; Spectrochimica Acta Part A 51; pp. 2101-2106; May 3, 1995.

Jastrzebska, M., et al "Raman spectroscopic study of glutaraldehyde stabilized collagen and pericardium tissue" Journal of Biomaterials Sciencem Polymer Editionm 14 (2) pp. 185-197, Apr. 2, 2003.

Jirasek et al.; "Accuracy and Precision of Manual Baseline Determination"; Applied Spectroscopy; 58012; pp. 1488-1499; 2004.

John, "A Wide-Angle View of Keratoconus," Review of Optometry, pp. 1-5, Oct. 2012.

Juhasz et al., "Time-resolved observations of shock waves and cavitation bubbles generated by femtosecond laser pulses in corneal tissue and water," Lasers in Surgery and Medicine, Jan. 1, 1996, vol. 19(1), pp. 23-31.

Juhasz, T., et al. "Corneal refractive surgery with femtosecond lasers," IEEE Journal of Selected Topics in Quantum Electronics, 5(4), 902-910 (1999).

Kanellopoulos AJ, et al "Epithelial Remodeling After Femtosecond Laser-assisted High Myopic LASIK: Comparison of Stand-alone With LASIK Combined With Prophylactic High-fluence Cross-linking" Cornea vol. 33 / Issue 5 May 2014 pp. 463-469.

Kanellopoulos AJ. "Collagen cross-linking in early keratoconus with riboflavin in a femtosecond laser-created pocket: initial clinical results." J Refract Surg. 2009;25:1034-1037.

(56) References Cited

OTHER PUBLICATIONS

Esmonde-White et al., "Fiber-optic Raman Spectroscopy of Joint Tissues", Analyst. vol. 136, No. 8, Apr. 21, 2012 (retrieved on Oct. 4, 2017). Retrieved from the Internet.
International Search Report and Written Opinion for International Application No. PCT/US2017/036915 dated Oct. 23, 2017.
Spoerl et al., "Induction of cross-links in corneal tissue", Experimental Eye Research, Jan. 1, 1998, vol. 66(1), pp. 97-103.
Wang et al., "Quantitative Raman Characterization of Cross-linked Collagen Thin Films as a Model System for Diagnosing Early Osteoarthritis", Proceedings vol. 9704, Biomedical Vibrational Spectroscopy 2016: Advances in Research and Industry, 970415, Mar. 7, 2016 [retrieved on Oct. 4, 2017], Retrieved from the Internet.

* cited by examiner

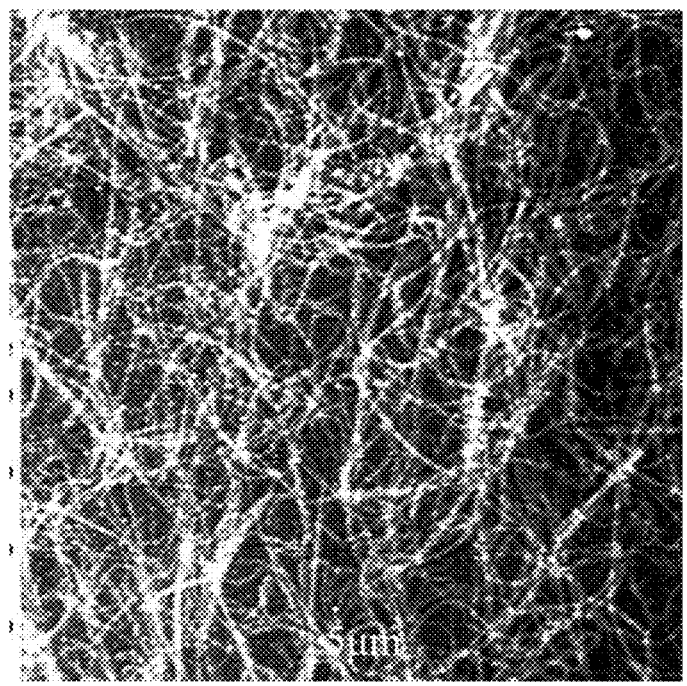
Fig. 2A
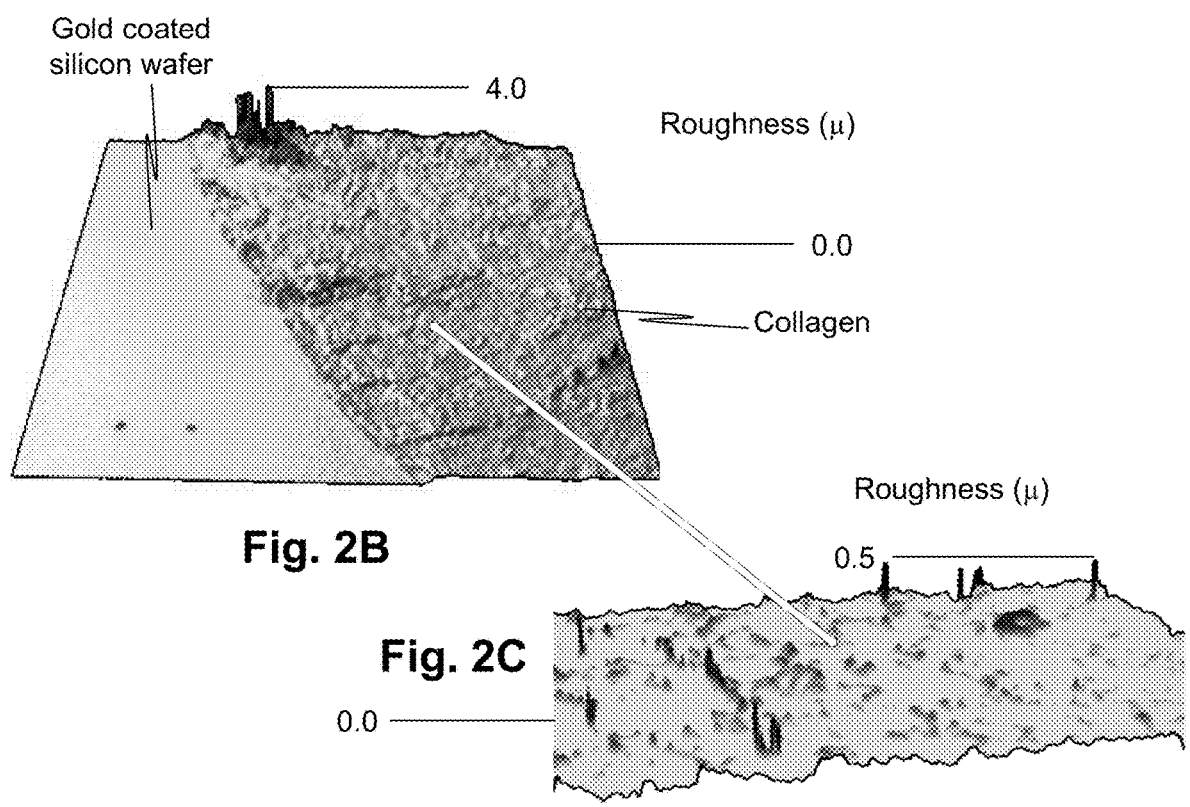
Fig. 2B
Fig. 2C

DEVICES, METHODS, AND SYSTEMS FOR DETECTION OF COLLAGEN TISSUE FEATURES

CROSS REFERENCE TO RELATED APPLICATIONS

This Application is a U.S. national stage filing under 35 U.S.C. § 371 of International Application No. PCT/US2017/036915, filed Jun. 10, 2017, which claims the benefit of U.S. Provisional Application No. 62/348,502, filed Jun. 10, 2016, each of which is incorporated herein by reference in its entirety.

BACKGROUND

Osteoarthritis (OA) is a progressive joint disease that severely affects articular cartilage. OA remains asymptomatic until its late stage, when the treatment options are limited to major interventions such as joint replacement. In adults, articular cartilage is an avascular connective tissue comprised of chondrocytes and collagenous extracellular matrix (ECM). Its main function is ensuring smooth joint movement and shock absorption. The ECM structure consists predominantly of collagens (COL) and proteoglycans (PGs), with the COL matrix providing tensile strength, whereas PGs resist compression. Initiation of OA could be caused by mechanical damage (trauma), proteolytic action secondary to soft-tissue injuries, or slow, age-dependent progression. Regardless of the initiation mechanism, an imbalance in ECM homeostasis is a key pathogenic pathway of OA. This imbalance results in progressive degradation of the ECM cartilage components. The onset of OA in articular cartilage is characterized by degradation of the ECM. Specifically, breakage of cross-links between collagen fibrils in the articular cartilage leads to loss of structural integrity of the bulk tissue.

SUMMARY

The present application discloses methods, devices, and systems for generating spatially-resolved quantification of cross-linking in cartilage based on Raman scattering of excitation light. The examples presented demonstrate that the method provides a discriminating power sufficient to distinguish early onset of osteo-arthritis even before a patient is symptomatic.

Objects and advantages of embodiments of the disclosed subject matter will become apparent from the following description when considered in conjunction with the accompanying drawings.

BRIEF DESCRIPTION OF THE DRAWINGS

Objects and advantages of embodiments of the disclosed subject matter will become apparent from the following description when considered in conjunction with the accompanying drawings.

FIG. 2A is an illustration for background showing collagen fiber polymerization level assessed with atomic force microscopy.

FIGS. 2B and 2C illustrate surface morphology and quantify roughness of samples used for experiments with collagen samples described herein.

In FIG. 6A, two maps are shown, one for control and one for a thin film exposed to 0.05% glutaraldehyde solution for 1 hour.

In FIG. 6B, two maps are shown for a thin film exposed to 0.05% glutaraldehyde solution, the top for 1.5 hour and the bottom for 2 hours.

In FIG. 6C, three maps are shown for a thin film exposed to 0.05% glutaraldehyde solution, the top for 2.5 hours, the middle for 3 hours, and the bottom for 4 hours.

In FIG. 6D, two maps are shown, one for control and one for a thin film exposed to 0.1% glutaraldehyde solution for 1 hour.

In FIG. 6E, two maps are shown for a thin film exposed to 0.1% glutaraldehyde solution, the top for 1.5 hour and the bottom for 2 hours.

In FIG. 6F, three maps are shown for a thin film exposed to 0.1% glutaraldehyde solution, the top for 2.5 hours, the middle for 3 hours, and the bottom for 4 hours.

In FIG. 6G, two maps are shown, one for control and one for a thin film exposed to 0.2% glutaraldehyde solution for 1 hour.

In FIG. 6H, two maps are shown for a thin film exposed to 0.2% glutaraldehyde solution, the top for 1.5 hour and the bottom for 2 hours.

In FIG. 6J, three maps are shown for a thin film exposed to 0.2% glutaraldehyde solution, the top for 2.5 hours, the middle for 3 hours, and the bottom for 4 hours.

DESCRIPTION OF THE PREFERRED EMBODIMENTS

Figure 1A:
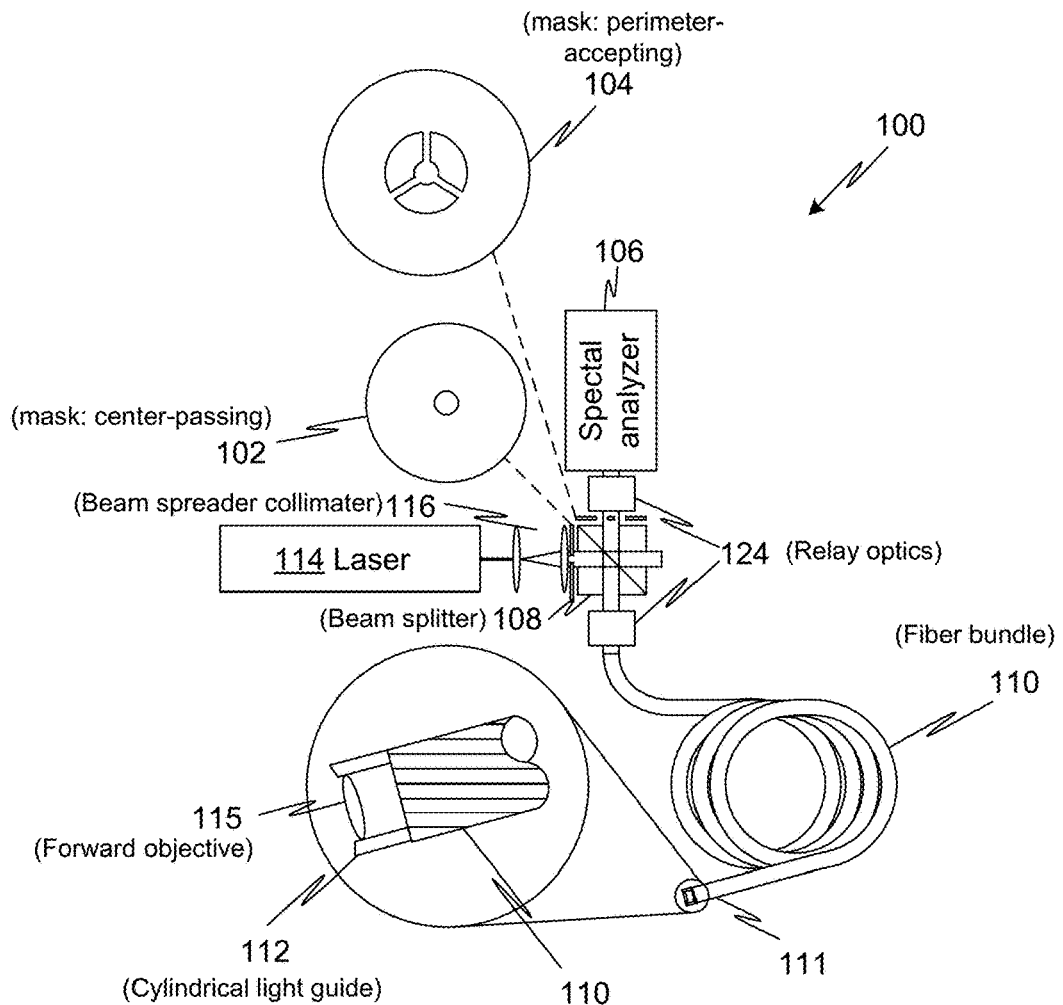
FIG. 1A shows an endoscopic detection and diagnostic instrument according to embodiments of the disclosed subject matter.

The present disclosure describes a quantitative diagnostic tool for detecting OA at its early stages, which may be a prerequisite for development of an effective treatment that does not require joint replacement. Accordingly, there is a need for non-invasive, label-free tools for diagnosing OA at its early stage.

Osteoarthritis (OA) affects millions of Americans: it is a progressive, complex, multi-tissue joint disease with degenerative changes in the articular cartilage and subchondral bone (1), with a long asymptomatic early development and debilitating late stages. Late-stage treatment options are limited to major interventions, including joint replacement; none of the early treatment modalities offer conclusive relief to patients. Despite the significant research and clinical effort dedicated to OA, there are currently no broadly accepted quantitative diagnostic tools for the early stages of the disease. Diagnosis and therapeutic interventions at the early stage of OA offer the promise of preventative care that could provide significant benefits to patient's quality of life.

Collagen is the major structural protein of most connective tissues. It provides the structural support to resident cells in the form of extracellular matrix (ECM). Many types of collagen have been identified, with the five most common types being Type I (e.g., as found in skin, tendon, vascular ligature, organs, bone), Type II (e.g., as found in cartilage), Type III (reticulate), Type IV (e.g., forming basal lamina), and Type V (e.g., cell surfaces, hair and placenta).

The structural integrity and mechanical properties of collagen-based joint tissues is significantly affected by collagen cross-links (CxL), chemical compounds that both, connect COL fibrils as well as molecules within the COL. It has been reported that degradation of the COL CxLs compromises structural integrity of articular cartilage, which may be lead to onset of OA. In a model, β-aminopropionitrile (BAPN) was used to block the formation of pyridinoline (PYD) CxLs in an immature bovine articular cartilage explant model. In a cartilage explant model, levels of glucose, cortisol and insulin were controlled in a serum-free, chemically defined media to investigate the evolution of biochemical and mechanical properties of live immature bovine cartilage. In this model cartilage explants lost their structural integrity in the absence of cortisol. The loss of structural integrity can be a result of degradation of CxLs in ECM. Therefore, the present disclosure proposes a method using Raman scattering capable of quantifying CxL concentrations in articular cartilage, which can advantageously be used to detect early onset OA.

Raman scattering is the process in which a small fraction of incoming photons, provided by a light source, inelastically collide with target molecules. As a result, the optical frequency of the outgoing photons is different from the incident photonic frequency, with the difference being equal to the vibrational energy of the scattering molecule. Raman spectroscopy allows investigation of functional groups and bonding types, providing information about the biochemical composition of tissues on a molecular level.

Raman micro-spectroscopy is a non-destructive and highly versatile analytical technique the exhibits vast potential for in vivo probing and in vitro analysis of biological tissues, especially as it does not require specimen preparation. However, the weakness of the signal, which is often masked by overwhelming fluorescence, has prevented a more widespread use of Raman scattering in the past. The use of infrared lasers as a light source, as well as advances in CCD detectors, have significantly improved the signal-to-noise ratio, enabling the use of Raman spectroscopy in probing tissues.

Analysis of Raman spectra obtained from articular cartilage has been challenging, and so far there is no generally accepted quantitative analysis for diagnosing early stages of OA. Thus, there is a need for methods of analyzing tissue for evaluating the presence of early stages of OA.

In one aspect, the present disclosure provides a method of analyzing mammal cartilage tissue, including generating a Raman spectrum of cartilage tissue; and measuring one or more Raman spectrum peaks corresponding to a cartilage crosslinking moiety. The cartilage may be articular cartilage and, in particular, the cartilage tissue may include collagen type I (COL I) or collagen type II (COL II).

In another aspect the cartilage tissue is of a patient with osteoarthritis, in particular early stage osteoarthritis.

The Raman spectrum may be generated using various Raman techniques and instruments. For example, the Raman spectrum is generated using Raman micro-spectroscopy, selective-sampling Raman micro-spectroscopy, coherent anti-Stokes Raman spectroscopy (CARS), stimulated Raman spectroscopy (SRS), surface enhanced Raman spectroscopy (SERS), surface enhanced resonance Raman spectroscopy (SERRS), spatially offset Raman spectroscopy (SORS), surface enhanced spatially offset Raman spectroscopy (SESORS), or transmission Raman spectroscopy (TRS).

Preferably, the Raman spectrum is generated in vivo, more preferably by endoscopy or arthoscopy, and even more preferably the Raman spectrum is generated using a fiber optic Raman probe. The fiber optic Raman probe may be a handheld probe.

The crosslinking moiety may be any moiety establishing crosslinks within the collagen, preferably between collagen fibrils in the cartilage. The crosslinking moiety may contain a central pyridine ring with substituents attached that are suitable for crosslinking. Examples of crosslinks include pyridinium-type crosslinks and pyridinoline crosslinks. In a preferred embodiment, the crosslinking moiety contains a pyridinium ring or pentosidine. Preferably, the crosslinking moiety is pyridinoline (i.e., hydroxylsylylpyridinoline).

In an embodiment of the present disclosure, COL thin films were used as a simplified model of collagenous extracellular matrix found in articular cartilage. Raman spectroscopy was used to assess changes of the relative concentration of CxLs induced by glutaraldehyde fixation. To achieve this goal, a quantitative method was developed whereby the relatively complex Raman signal obtained from the collagen was decomposed into known chemical structures and their allowable vibrational modes. Each of the structures was then modeled as a mathematical function and their sum forms an optimization function that produces model of the spectra via curve fitting. Relevant information on the CxLs was then extracted from the model. Quantitatively assessing relative CxL concentrations in articular cartilage is proposed as an avenue for diagnosing early stage OA in an embodiment.

In an embodiment taking place in a clinical setting, a patient may be subjected to arthroscopy with a fiber optic Raman probe inserted into articular cartilage. A Raman spectrum is generated and analyzed for peaks corresponding to cartilage crosslinking moieties, thereby facilitating diagnosis of OA, in particular early stage OA.

Figure 1B:
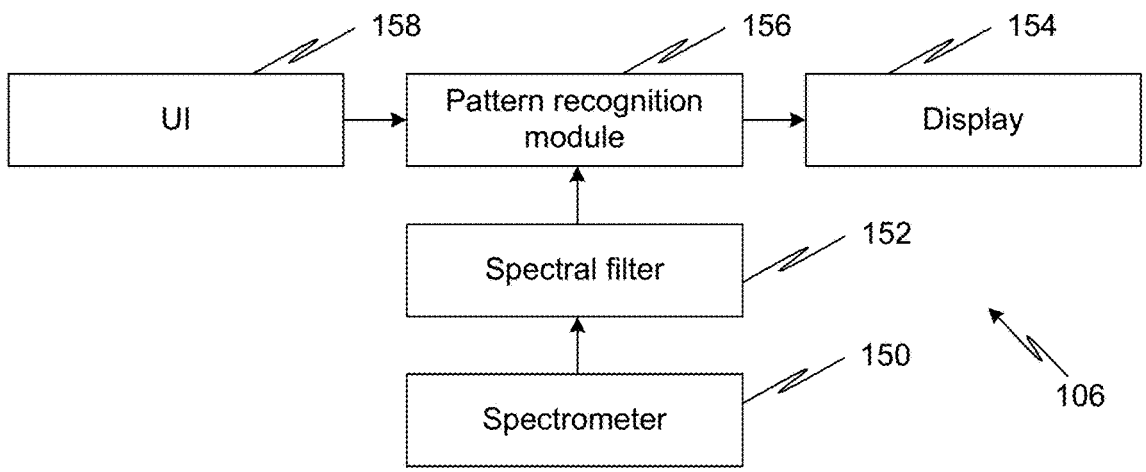
FIG. 1B shows a signal filtering and classification component of the instrument of FIG. 1A.

FIGS. 1A and 1B show features of an endoscopic instrument as an example of a diagnostic tool for distinguishing health from diseased tissue according to embodiments of the disclosed subject matter. FIG. 1A illustrates an endoscopic tissue inspector 100 that transmits excitation light from a light source such as a laser 114 to a sample and receives and relays scattered light from the sample to a spectral analyzer 106. A probe 111 is used for delivery of excitation light and collection of a Raman signal. A fiber bundle 110 connects the probe 111 to a laser excitation source 114. The central fibers of the fiber bundle 110 convey the excitation light and perimeter fibers of the fiber bundle 110 convey received light from a sample to a spectral analyzer 106 which may contain a spectrometer (e.g., Horiba iHR320). An incisions may be made in the tissue of a patient as part of a surgical procedure or for diagnosis. The probe 111 may be inserted through the incision and positioned at one or more locations near the edge of an articular cartilage or other connective tissue to generate and receive a return light signal. A separate probe or one that is collinear with probe 111 may be used to image the scene inside the incision to guide the probe 111. In alternative embodiments multiple probes may be used, one for delivering excitation light and one for receiving light from the sample.

The spectral analyzer 106 may include a spectrometer 150 which receives light from a fiber bundle 110 and generates a digital representation of the spectrum of the received light. The latter may be applied to a spectral filter 152, for example which may notch out irrelevant portions of the spectrum, quantify certain peaks, or otherwise reduce the dimensionality of the information in the spectrum so that only predefined features (a feature vector) of the spectrum are applied to a pattern recognition module 156. The patter recogniation module 156 may be a computer running a program that distinguishes feature vectors characteristic of healthy tissue from feature vectors characteristic of diseased tissue. For example, the intensities of certain spectral peaks may indicate the quantity of features of cross-links in articular cartilage which further may discriminate arthritic from non-arthritic tissue as described below. The magnitudes of the spectral peaks and a symbol indicating a probability estimate for assigning a current sample to the class of diseased or healthy tissue may be output on a display 154. A user interface 158 may be used to program the pattern recognition module.

Light may be transmitted from a laser 114 according to embodiments disclosed in the experimental examples described above or others. The beam of the laser 114 may be conditioned using a variety of optical devices to form a beam whose width corresponds to the diameter of a predefined fiber bundle 110. Note that, as will be evident from the further description, the fiber bundle 110 may be replaced by a pair of concentric light pipes as will be evident from the further disclosure or by two concentric fiber bundles separated by a concentric spacer. The widened beam emerging from a beam spreader 116 is masked by a pinhole 102 that passes light such that only the central fibers carry light toward a forward objective 115. The light from the pinhole 102 (note that despite the use of the term pinhole, it should be evident that the size of the hole is not restricted) passes to a beam splitter which allows the excitation light (from the laser 114 and pinhole 102) to be collinear along the fiber bundle with signal light from a sample returning along the concentric outer fibers of the fiber bundle 110. The reflected light is relayed by relay optics 124 to the end of the fiber bundle which is precisely positioned such that only the central fiber (or fiber) carry light toward the target. Excitation light is focused by a forward objective 115 (here figuratively shown as a single lens but in practice it would be a multi-element component with a high numerical aperture. Light scattered from the sample due to the excitation light is received by a cylindrical light guide 112 having a beveled surface and configured to accept light from multiple angles. The light guide 112 transmits received light to the outer fibers surrounding the central ones in the fiber bundle 110. Received light, including light from Raman scattering in the tissue sample passes through the relay optics 124 and beam splitter 108, masked by the perimeter accepting mask 104, and received by a spectrometer of the spectral analyzer 106.

Figure 1C:
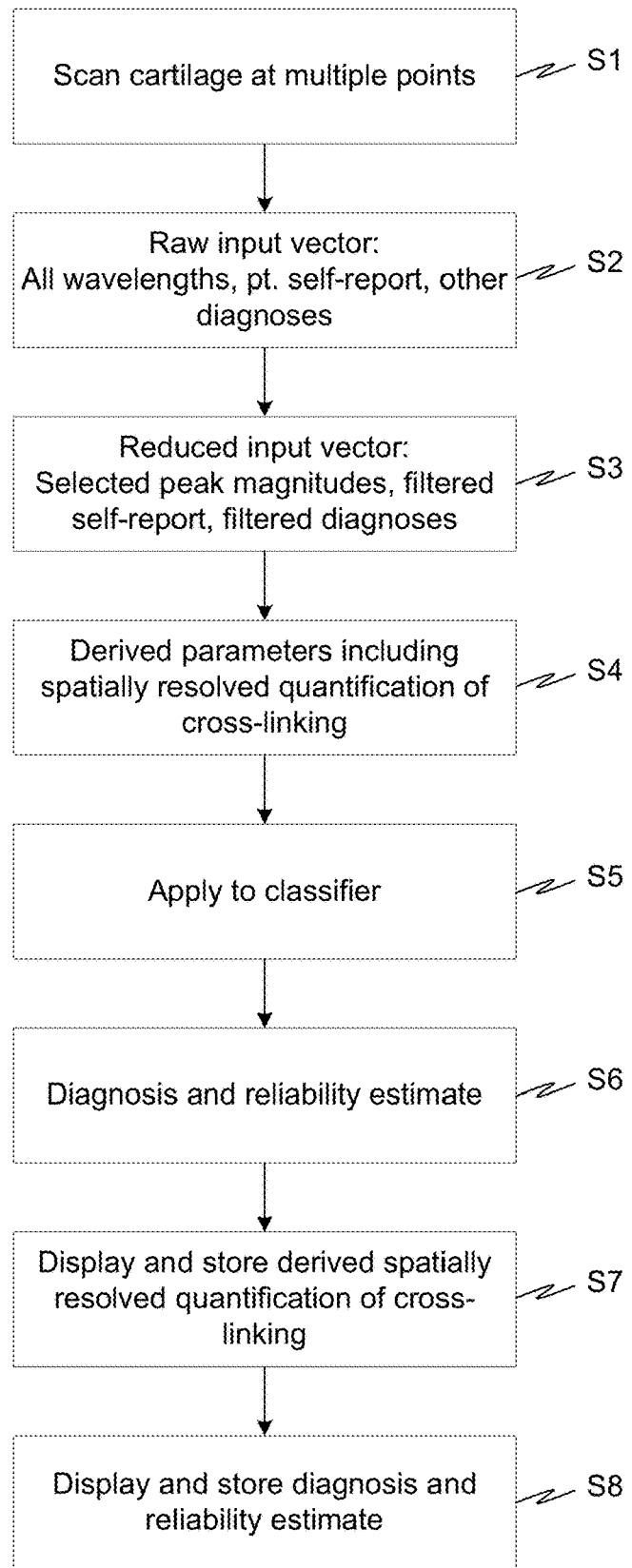
FIG. 1C shows a method for diagnosing arthritis in a cartilage, according to embodiments of the disclosed subject matter.

Referring to FIG. 1C, in a method implemented by an embedded or host processor (See FIGS. 1A, 1B), a cartilage is scanned as described above to acquire Raman samples at one or more locations of the cartilage. S1. A raw input vector may be generated that includes the raw Raman signal and other data such as patient record data including other conditions or diseases of the patient. S2. A reduced input vector may be constructed by filtering the Raman samples, for example, detecting magnitudes of one or more spectral peaks. S3. From the reduced Raman data, at S4, the degree of cross-linking may be quantified. In embodiments, the magnitude of cross-linking may show a distribution of magnitudes. At S5, the reduced input vector is applied to a classifier. At S6, a class is output as a diagnosis along with a reliability estimate. The classifier may be a software implementation that is as simple as thresholding an average magnitude of Raman spectral peak(s) or a more sophisticated model that takes account of the distribution of the magnitudes of cross-linking. At S7, the class is output and spatially-resolved cross-linking maps may be output. At S8, the diagnosis may be output on a display.

EXAMPLES

Sample Preparation

In an embodiment, neutralized collagen solution (PH 7.4) was prepared from 3.1 mg/ml type I collagen from bovine hides (PureCol, Advanced Biomatrix San Diego, Calif., USA) in 10× Dulbecco's phosphate buffered saline (DPBS) and 0.1 M NaOH. Neutralized COL solutions were applied on alkanethiol treated gold-coated silicon wafers to produce thin films. Before being used to prepare thin films, the substrates were cut into 15 mm×15 mm pieces and placed in petri dishes. Silicon substrates were coated with a 5 nm layer of chromium and 18 nm layer of gold through thermal deposition (Edwards BOC/Auto 306 Thermal Evaporator) and rinsed with ethanol. Coating was introduced to reduce fluorescence background to the Raman spectra. 1.8 ml of the neutralized COL solution was applied onto a coated silicon wafer in a petri dish and then incubated at 37° C. for 12 h.

After incubation, the samples were immersed in 1-hexadecanethiol (0.5 mM; Sigma Aldrich) ethanol solution for 8 h prior to being rinsed with ethanol and dried with filtered Na. Incubated collagen was rinsed with 1×DPBS and deionized $H_2O$ 10 times to remove the bulk salt and gels from the surface. After rinsing, specimens were immediately placed in DPBS (1×) and stored at 4° C. Prior to treatment/ characterization, samples were taken out of the DPBS, rinsed with deionized $H_2O$ and dried with a filtered nitrogen gun.

The degree of fiber polymerization of thin films was assessed via atomic force microscopy (PSIA XE-100 AFM (Park Systems, Santa Clara, Calif., USA), whereas thickness and surface uniformity were characterized with optical profilometer. See FIGS. 2A-2C.

Glutaraldehyde (GA) solution, being a known cross-linker was used to introduce various levels of collagen cross-links. Varying exposure and concentration of GA solution controlled CxL concentration levels. Three batches of samples were treated with GA concentrations of 0.05%, 0.1% and 0.2%, respectively. There were seven samples within each batch, fixation times were 1 h, 1.5 h, 2 h, 2.5 h, 3 h and 4 h. 5 ml of GA solution was applied onto each sample. After the fixation cross-linked COL films were rinsed with deionized water and desorbed into 20 ml PBS (0.2 M, PH 7.4, Sigma Aldrich) for 48-72 h. Subsequently, specimens were rinsed with deionized $H_2O$ and DPBS (1×) several times, stored in DPBS(1×) at 4° C. and kept sterile. Cross-linked COL thin films were rinsed with deionized $H_2O$ prior to Raman characterization.

Raman Characterization

Raman spectra were acquired with a confocal microspectrometer (InVia, Renishaw Wotton-under-Edge, Gloucestershire, UK). Incident laser excitation was provided by helium-neon laser with 632.8 nm wavelength, delivered by 100× objective. Spectral resolution provided by 1800 gr/mm diffraction grating was 1 $cm^{-1}$.

Raman signal was acquired with 10 accumulations, each lasting 10 s. Prior to the acquisition of the spectrum at each measurement point, photobleaching was applied for 10 s to reduce the fluorescence background. Spatially resolved characterization was performed to generate spectral maps. A 57 mm×30 mm window within each sample was assessed and each spectral map included 220 measurement points.

Computational implementation of the proposed model was carried in MatLab (Mathworks, Inc) as a two-step process, each requiring curve fitting of experimental data. First, the signal was pre-processed to remove fluorescence background and then relevant segments of Raman spectra were modeled. Fluorescence is commonly removed by fitting the region of the spectra below distinctive Raman bands with low order polynomial function. Fluorescence was iteratively fitted with a fifth order polynomial and subsequently subtracted from the raw signal. In the second step, the vibrational modes of interest were approximated as a damped harmonic oscillator driven by a force whose profile follows a sinusoidal curve. According to the hydrodynamic theory, Raman lines naturally follow a Lorentzian profile. Thus, the optimization function is the sum of Lorentzians. The trust region optimization model was employed for curve fitting of the Raman spectra. Conceptually, it is a maximum neighborhood method developed through interpolation between the Taylor series method and the gradient descent method. It sets a problem as the iterative solving of a set of nonlinear algebraic equations. However, if the initial estimate is too far from the optimum, the algorithm will not converge. Therefore, the subset of the region of the objective function is defined and optimized first. The function is approximated with a simpler one which reasonably reflects the behavior of the original function in a neighborhood E around the point x. This neighborhood is referred to as the trust region. In essence, the trust region represents constraints derived from the underlying biochemistry of the specimen.

Collagen in the ECM of articular cartilage is predominantly type II (COL II), whereas due to practical considerations the present model use type I (COL I). The major difference between COL I and COL II is a "phase shift" in their chains. In COL I the NH groups point counter-clockwise when viewed from the carboxyl ends of the chains, whereas in COL II the opposite is true. If an existing set of hydrogen bonds in COL I is broken, and each polypeptide chain rotated about its own axis by approximately $\pi/3$, the NH group would instead be attached to the carbonyl oxygen, forming the hydrogen bond.

Figure 3A:
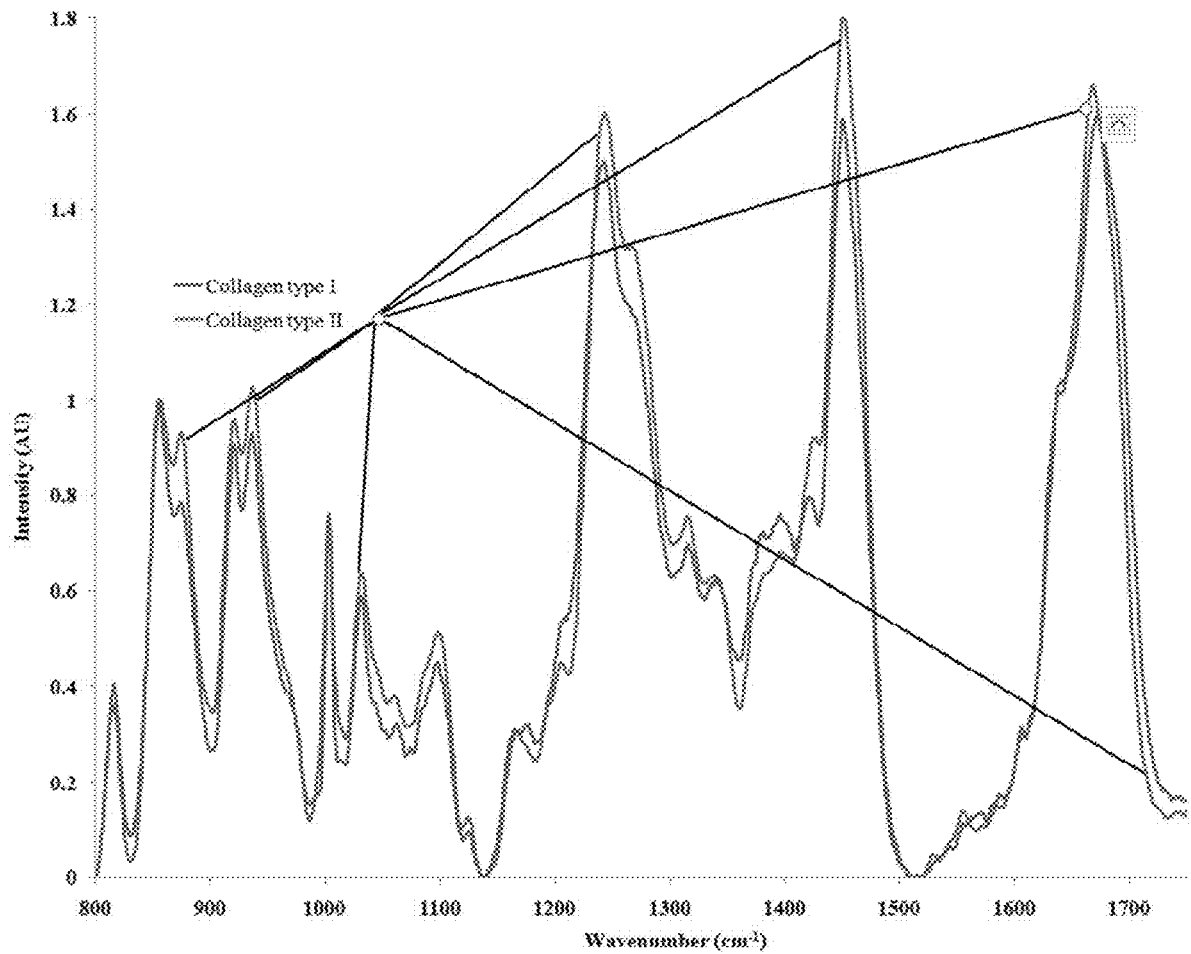
FIG. 3A shows normalized Raman spectra of COL I and COL II in superposition.

Consequently, Raman spectra of COL I and II are rather similar, as shown in FIG. 3A. Further, the proposed cross-link (CxL) concentration assessment relies on quantification of the concentration pyridine aromatic rings, which are centerpieces of bothpyridinium CxLs induced by GA-fixation in COL I and hydroxylysylpyridinoline (PYD) CxLs that are present in the COL II of the ECM of articular cartilage. The Raman band associated with in-plane stretching of pyridine ring is observed at the same location in the spectra of COL I and COL II (FIG. 3A) as well as in articular cartilage explants. The ring is a prominent CxL residue found in fibrillar COLs and most connective tissues, except cornea and skin.

Collagen is a large molecule comprised of three polypeptide chains, which form a right-handed triple helix. Each of the chains contains multiple regions of repeating amino acid sequences $(Gly-X-Y)_n$, where Gly is glycine and X and Y are often proline and hydroxyproline.

Figure 3B:
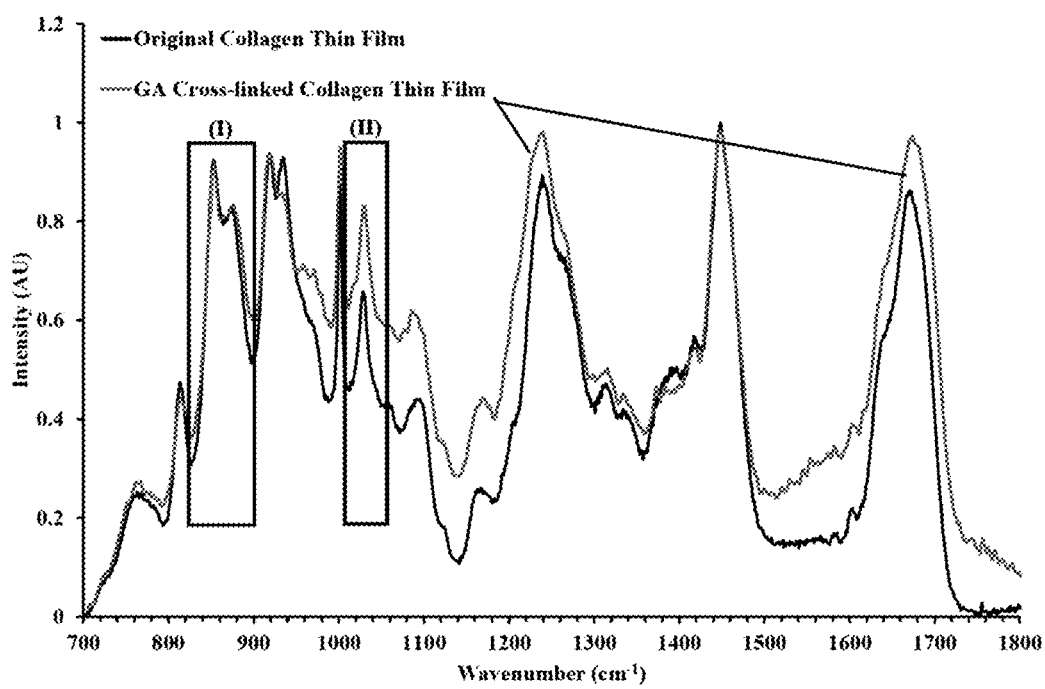
FIG. 3B shows a normalized Rama spectra of control and glutaraldehyde-fixed collagen thin films.

FIG. 3B depicts Raman spectra of collagen type I (COL I) obtained from a thin film sample, superimposed with the spectra of GA-treated COL I. The dominant Raman band at the far right side of the spectrum, centered at 1669 $cm^{-1}$, is assigned to amide I and in COL I is mainly attributed to carbonyl stretching of the peptide bond in the Gly-X-Y tripeptide sequence. Two superimposed Raman bands in the center of the signal, with peaks at 1240 $cm^{-1}$ and 1268 $cm^{-1}$, respectively represent coupling of CN stretching with NH in-plane deformation, and are assigned to amide III. The peak at 1240 $cm^{-1}$ is associated with proline rich regions, whereas 1268 $cm^{-1}$ corresponds to proline poor regions, respectively. Amide I and amide III, together with C—C stretching of the backbone formed by the Gly-X-Y sequence found at 935 $cm^{-1}$, suggest an α-helix conformation. Vibrations of the proline ring, specifically C—C stretching, is attributed to Raman bands centered at 853 $cm^{-1}$ and 918 $cm^{-1}$, and the hydroxyproline ring gives rise to Raman band with peak at 875 $cm^{-1}$. The isolated Raman band located at 1030 cm-1 is associated with C—C stretching of aromatic pyridine ring.

In an embodiment, GA treatment resulted in a shift of the amide I and amide III bands. The peak of the amide I bandshifted to 1674 $cm^{-1}$, and bands attributed to Amide III became centered at 1235 $cm^{-1}$ and 1264 $cm^{-1}$, respectively. In the spectra of GA-fixed samples, a new band appeared at 865 $cm^{-1}$ which is attributed to COC symmetric stretching. This band is due to ether-type COC CxL, which is a result of the reaction of the GA aldehyde group with the carbonyl group of the peptide bond in COL. Newly formed ether-type bond weakens hydrogen bonds, producing conformational modifications of the protein structure, which are seen as Raman shifts of the amide I and amide III bands. Quaternary pyridinium compounds form stable CxLs in GA-fixed samples. The 1030 $cm^{-1}$ band is due to in-plane deformation of six-membered aromatic ring and is an indicator of the 1, 3, 5-substituted pyridine ring, similar to the CxLs of interest in articular COL.

Figure 4A:
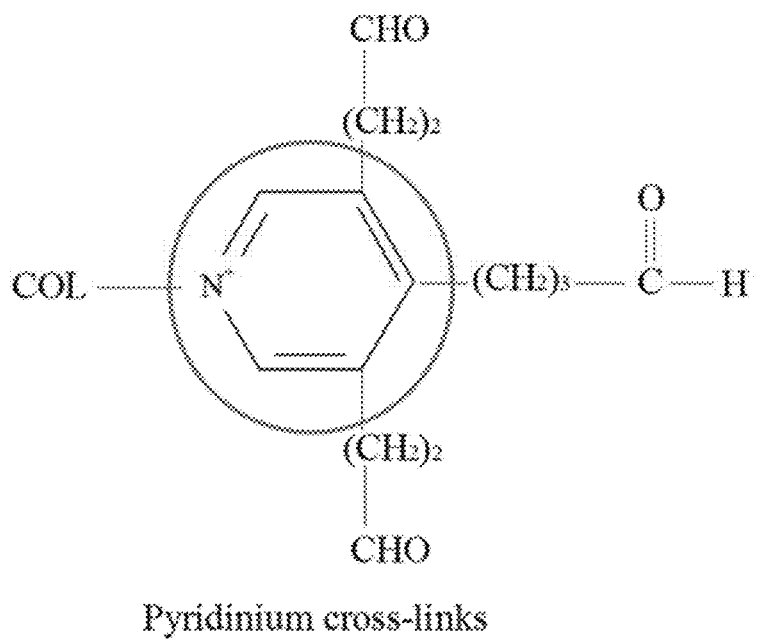
FIGS. 4A and 4B show the similarity between hydroxylysylpyridinoline, a major crosslink naturally occurring in articular cartilage and glutaraldehyde induced pyridinium-type crosslink schematic diagrams of hydroxylysylpyridinoline FIG. 4A and pyridinium-type crosslinks FIG. 4B. Central chemical compound in both crosslinks is pyridine ring.
Figure 4B:
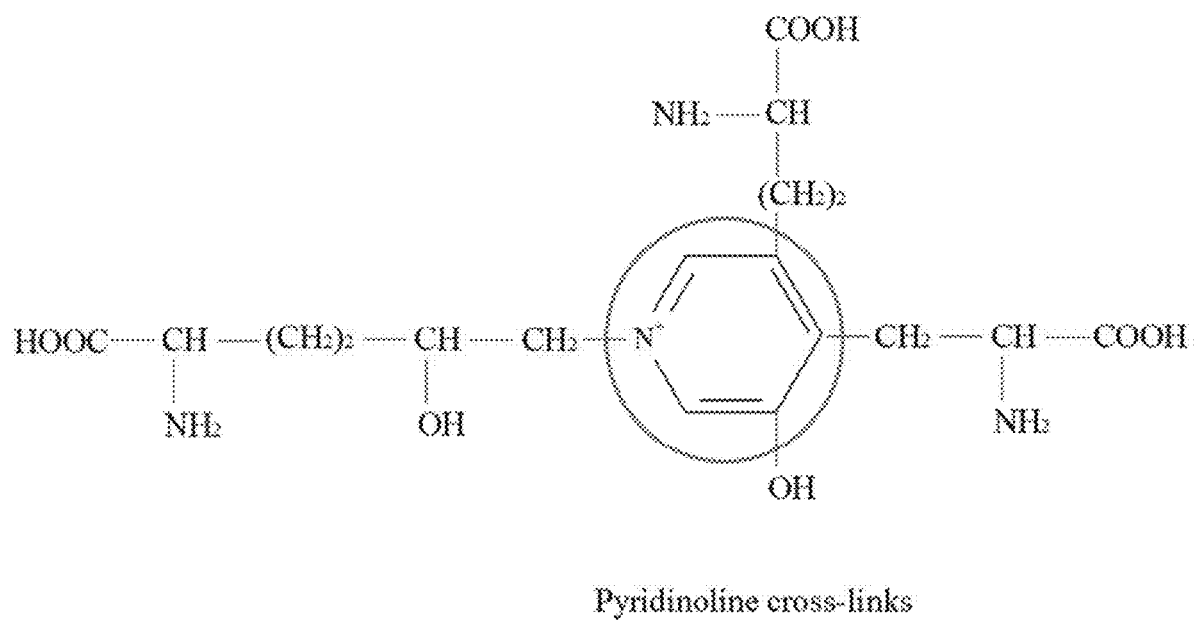
Figure 4C:
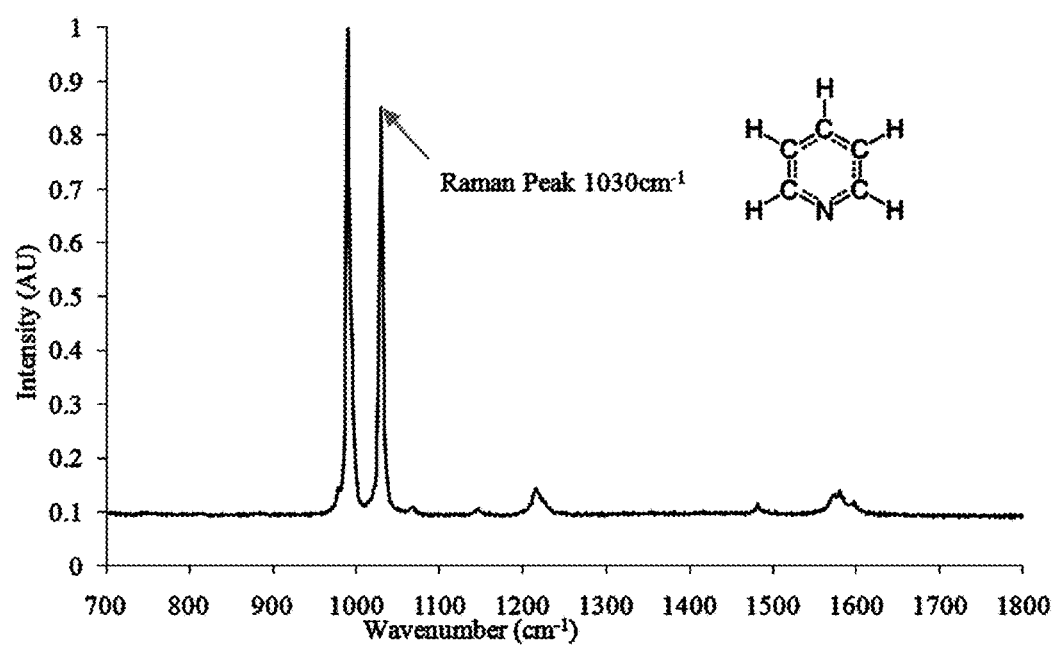
FIG. 4C is a Raman spectrum of pyridine.

Pyridinium-type CxLs in GA-fixed COL samples have a pyridine ring as their central feature whose vibrational modes are similar to monosubstituted six-membered rings. Similarly PYD, which is one of the major COL CxLs and is responsible for the tensile strength and structural integrity of cartilage ECM has a pyridine-like aromatic ring as its central chemical structure (FIGS. 4A and 4B). Assessment of relative concentration of pyridine rings in articular cartilage thus can provide information about the concentration of PYR CxLs. Stable vibrational modes of pyridine consist of in-plane ring deformation and symmetric ring breathing modes as shown in FIG. 4C. The former involves displacing alternate carbon atoms around the ring and is characterized by a rise of the 1030 $cm^{-1}$ band. The latter is attributed to symmetric ring stretching that involves all carbons and nitrogen moving in and out in unison. The Raman band associated with this mode is located at 992 $cm^{-1}$. The 1030 $cm^{-1}$ band is present in both purified COL (box II in FIG. 3B) and bovine articular cartilage explants. Furthermore, there is no significant overlapping of the Raman band centered at 1030 $cm^{-1}$ and other bands in the COL spectra, which simplifies the analysis to some extent.

Quantification of the changes in the relative concentration of pyridinium-type CxLs was achieved via modeling of the experimental data, which enabled the analysis of changes in individual Raman bands due to GA-fixation. It is assumed that the relative concentration of the pyridine rings within the focal volume is proportional to the normalized integrated intensity of the Raman band associated with in-plane ring deformation. Modeling of the spectrum was needed to assess contributions of the individual bands to the complex signal that is comprised of a relatively large number of overlapping Raman bands.

Subsequently, quantitative information about the particular Raman band of interest could be extracted from the model. By taking advantage of the additive property of the Raman signal, segments of interest in the COL Raman spectra (box I and box II in FIG. 3B) can be seen as the sum of the individual bands. Therefore, the optimization function, which is used to model the spectrum, is the sum of the functions describing individual bands. The concentration of CxLs is quantified as the area under the curve of the 1030 $cm^{-1}$ peak in the modeled spectrum, normalized by the area under the hydroxyproline curve assigned to COL. Normalization can help avoid errors which could arise as a result of concentration-dependent changes. The trust region optimization model used for these analyses, is an adaptive method that utilizes a two-step approach in which the approximation model predicts the improvement of the system being optimized before resorting to a detailed model that confirms the validity of the initial approximation, followed by constrained variation of the trust region. The modeling may include a locally constrained optimal step in the otherwise unconstrained approximate iteration. The underlying biochemistry, including the location of the peak assignments, helped to introduce appropriate constraints in the optimization model so that a unique solution could be obtained.

Figure 5A:
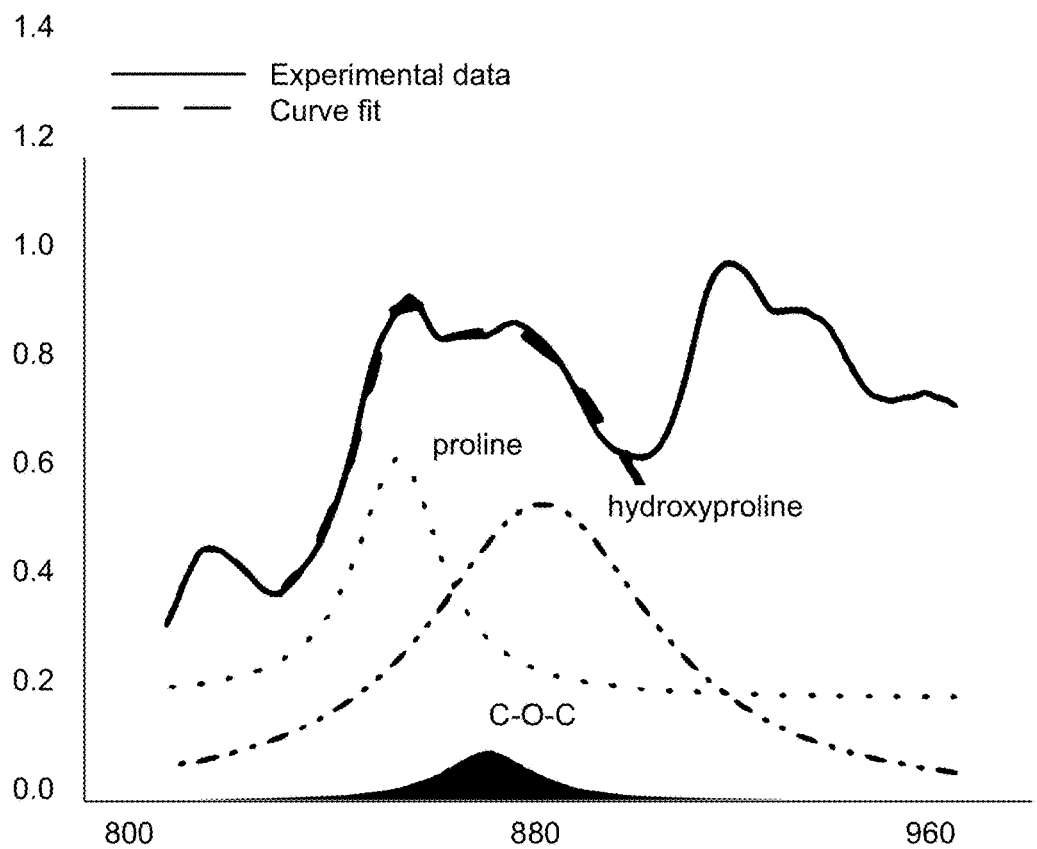
FIGS. 5A and 5B show decomposition modeling of segments of COL I Raman spectrum where FIG. 5A corresponds to the first outline box in FIG. 3B and FIG. 5B corresponds to the second (right side) outline box in FIG. 3B.
Figure 5B:
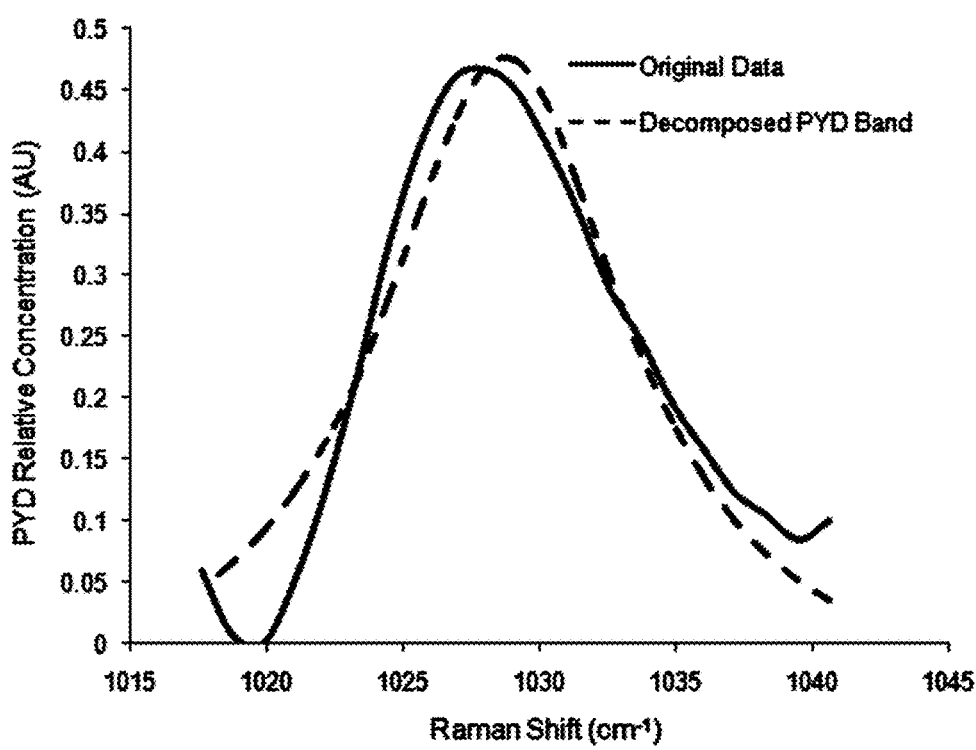
Figure 6A:
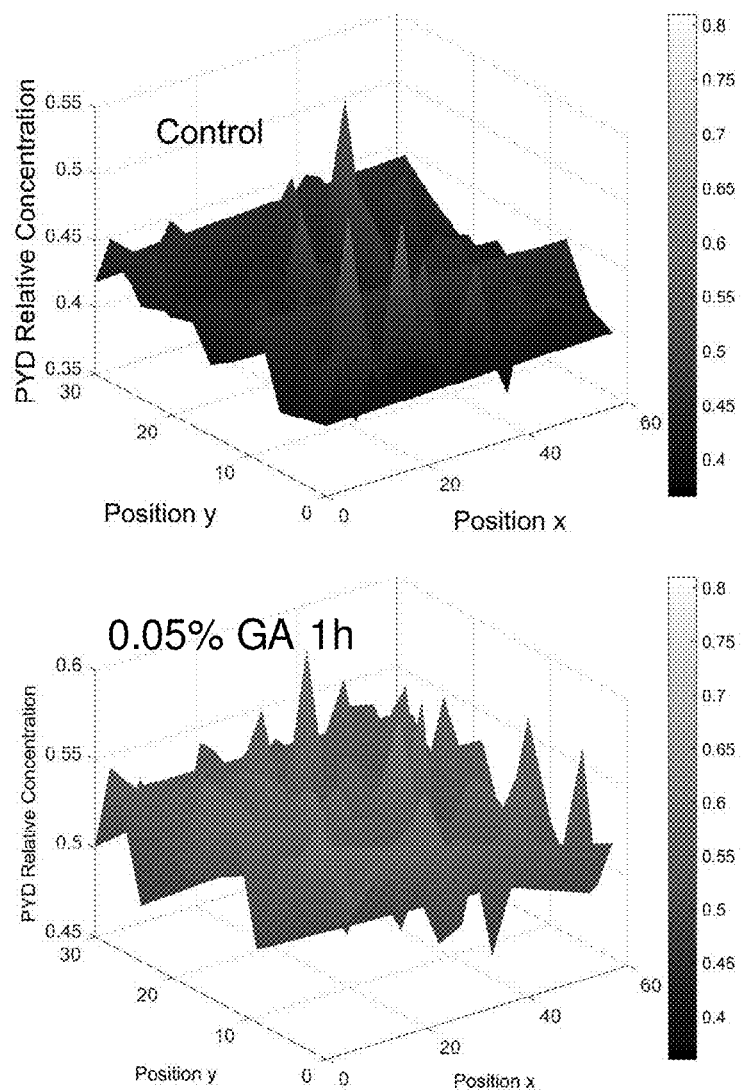
FIGS. 6A through 6H and 6J are spatially resolved spectral maps of the normalized integrated intensity (concentration) of the 1030 $cm^{-1}$ Raman band associated with the pyridinium type cross-linking.
Figure 6B:
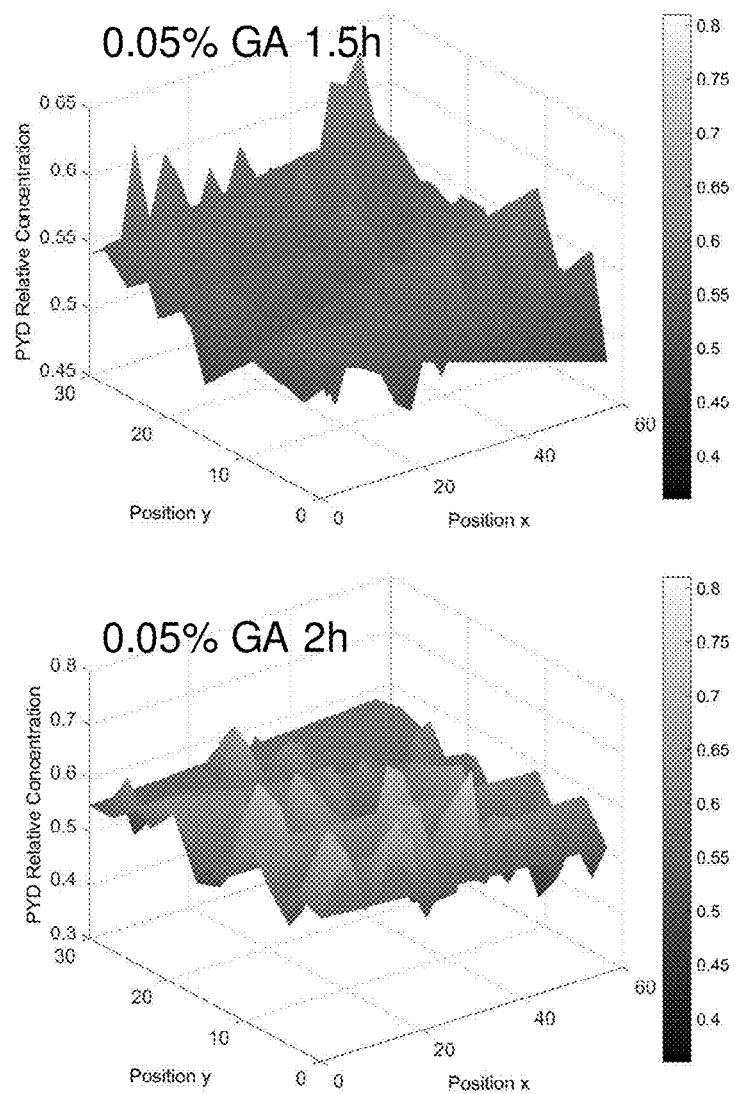
Figure 6C:
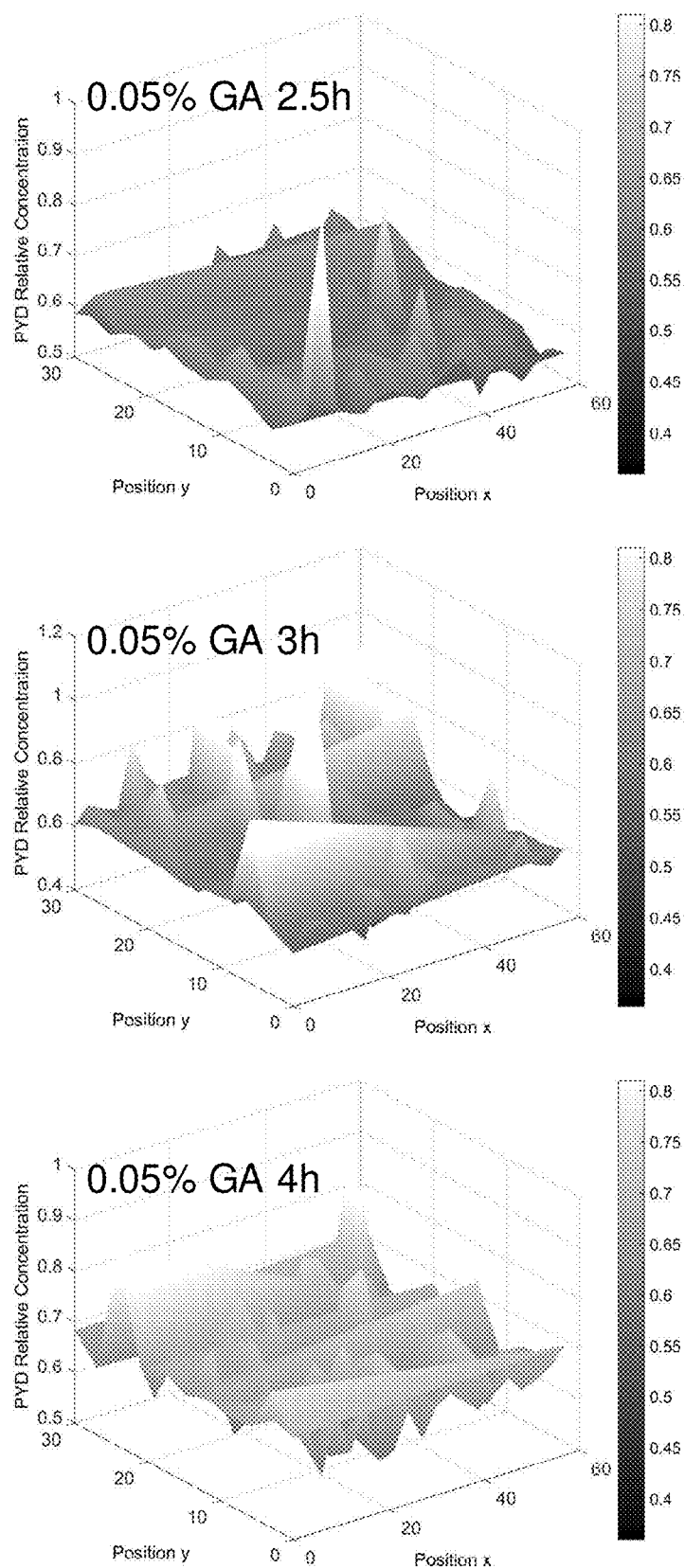
Figure 6D:
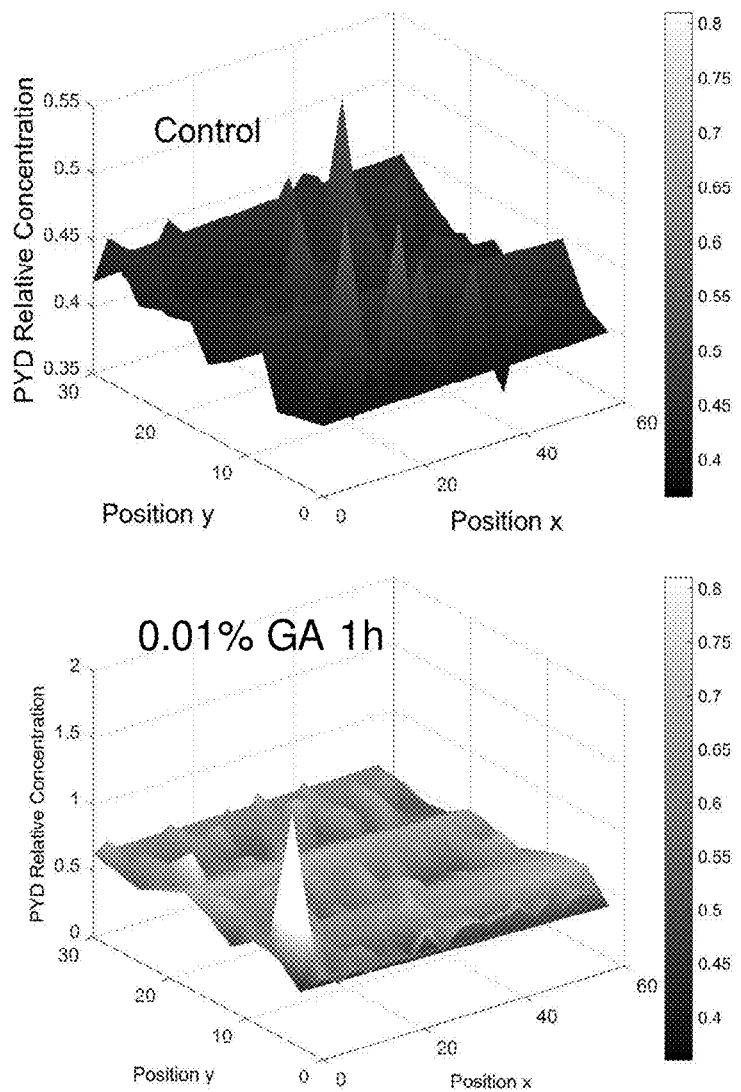
Figure 6E:
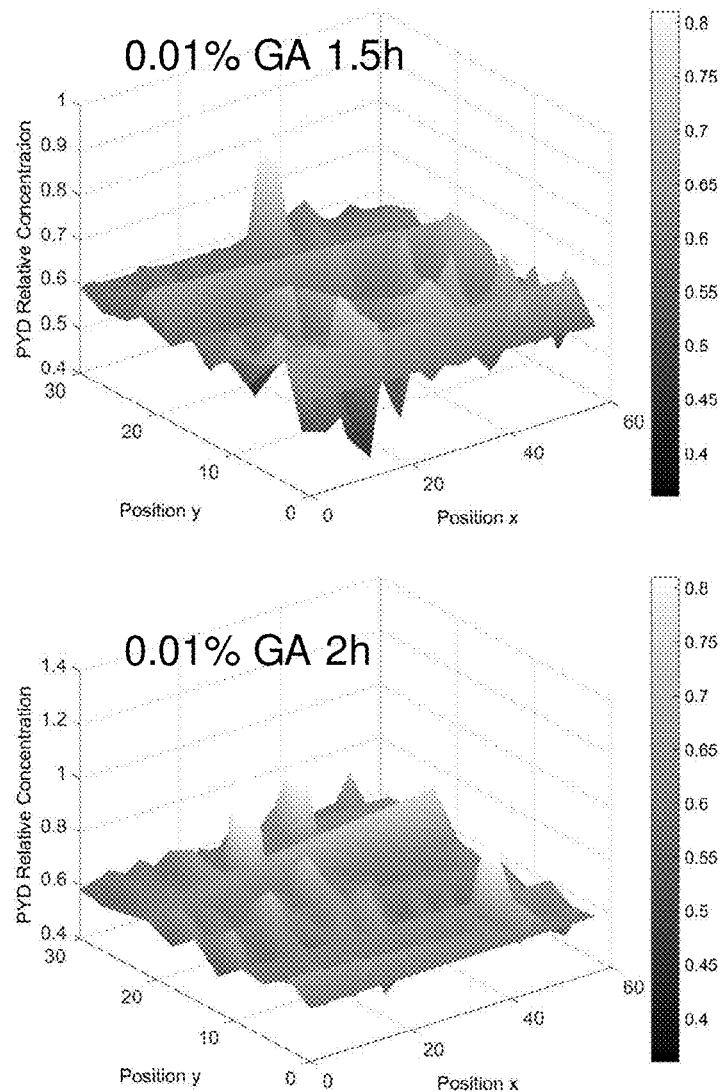
Figure 6F:
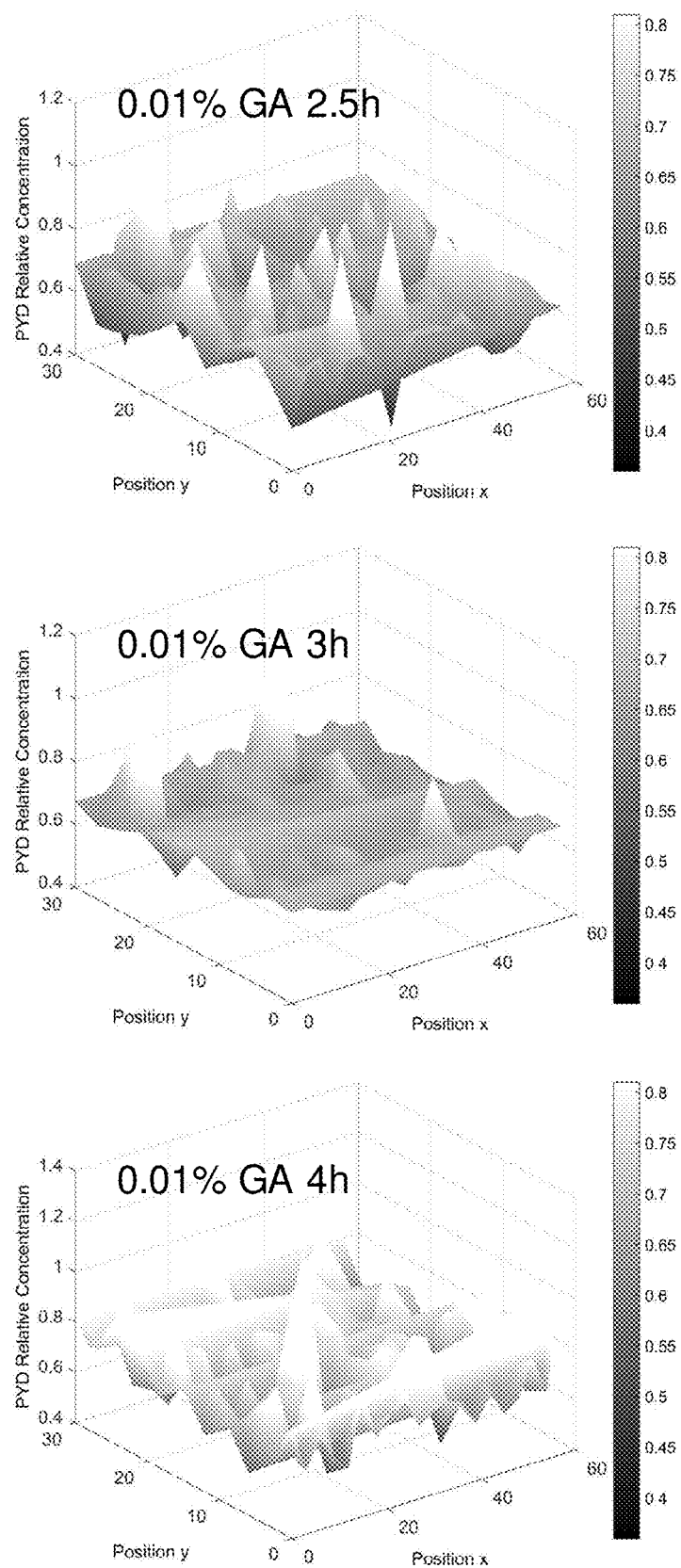
Figure 6G:
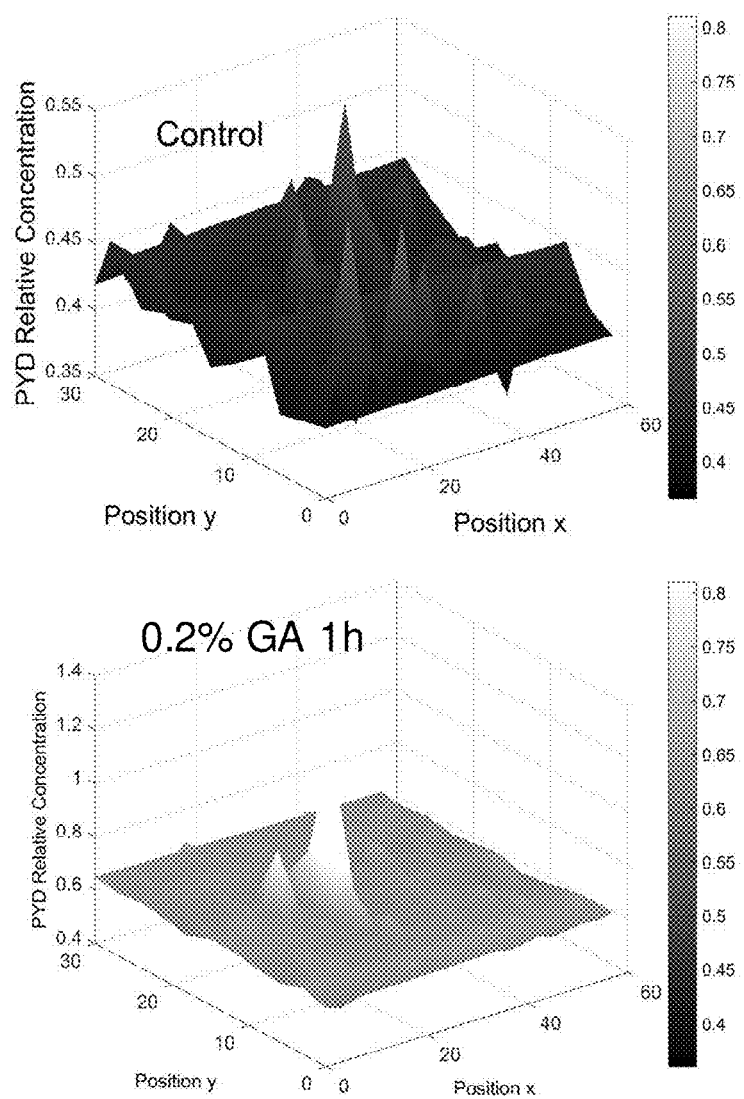
Figure 6H:
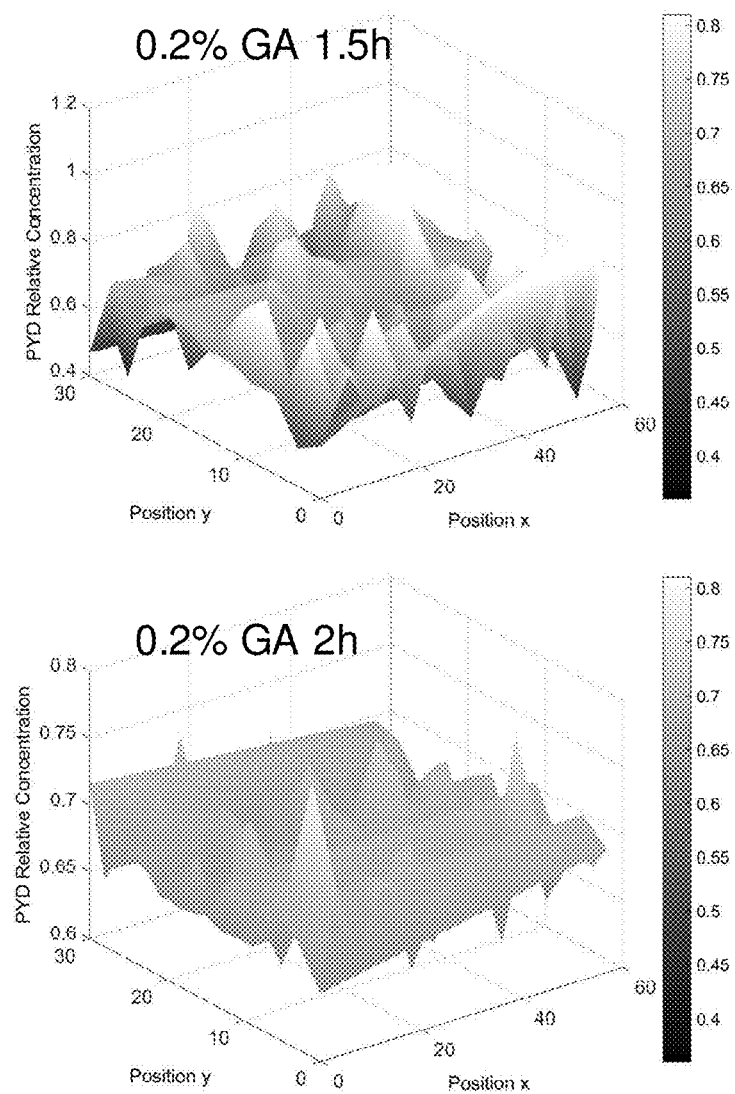
Figure 6J:
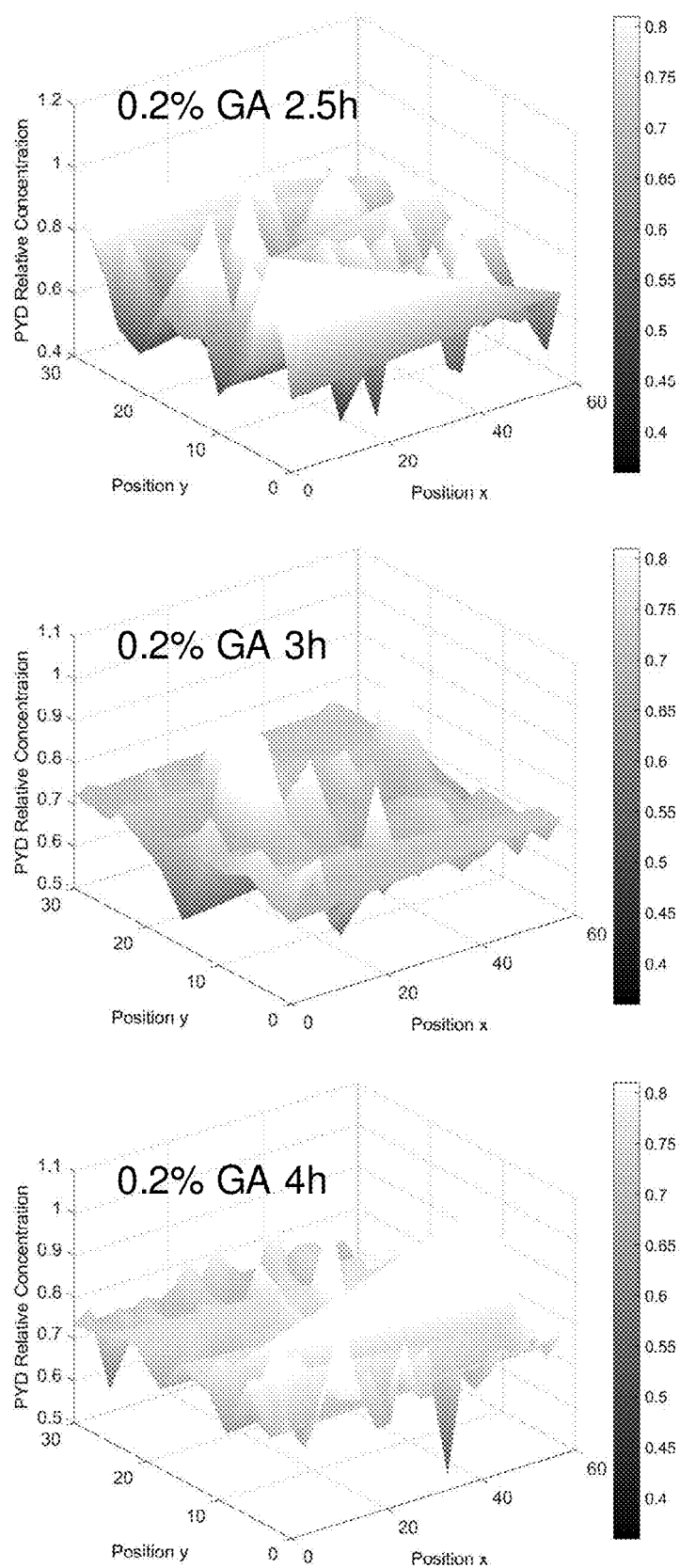

This approach yields a unique solution when treating large numbers of varying parameters, while being sufficiently sensitive to capture subtle changes in the vibrational spectra that arise from the potentially modest changes in the crosslink density. Two segments of the spectrum have been modeled, and the resulting modeled spectrum closely matches experimental data shown in FIGS. 5A and 5B. From the first segment the integrated intensity of the hydroxyproline band has been extracted and used to normalize the integrated intensity of the band centered at 1030 $cm^{-1}$, which is associated with in-plane stretching of pyridine rings.

Spatially resolved characterization of the COL thin films was utilized for generation of spectral maps shown in the non-limiting example of FIGS. 6A through 6J. Each spectrum in the map was modeled as outlined above and the integrated intensity of the 1030 $cm^{-1}$ band was utilized as a parameter that represents CxL relative concentration. Each map depicted in FIGS. 6A through 6J corresponds to a specimen subjected to GA fixation. It can be seen that an increase in the concentration of GA and prolonged exposure to GA both produce an increase in the relative concentration of pyridinium-type CxLs.

Figure 7:
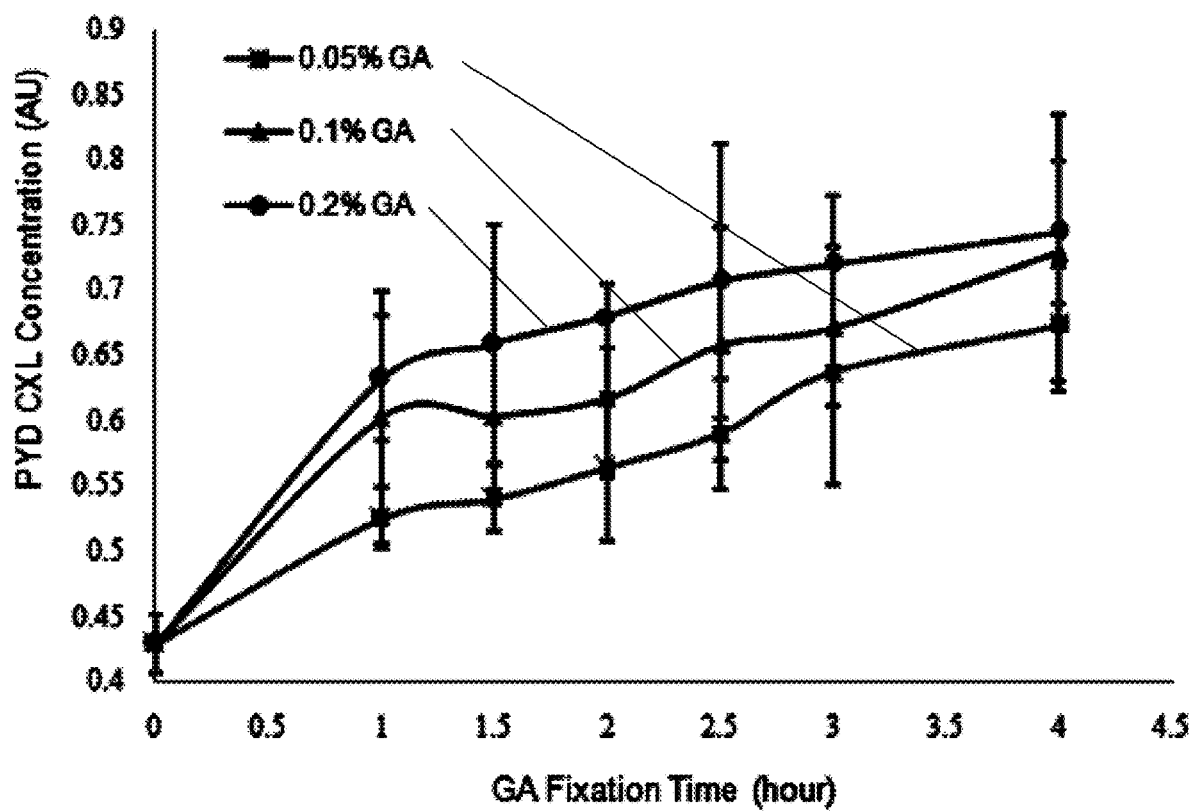
FIG. 7 shows averaged PYR-type cross-link concentrations for various concentrations of GA solutions. One way analysis of variants (ANOVA) was applied for data analysis.

Averaged values of CxL concentrations at different exposure times and GA concentrations are summarized in FIG. 7. COL thin films exposed to 0.05% GA experience a nearly linear increase in the relative CxL concentration, whereas specimens treated with 0.1% and 0.2% GA solution exhibit a higher rate of increase in the first hour of exposure, after which the increase rate slows down and becomes similar to that seen in samples fixed with 0.05% GA solution.

A collagen thin film model to simulate changes in relative crosslink concentration in extracellular matrix of an articular cartilage has been introduced. Samples were treated with varying concentrations of glutaraldehyde solutions at different exposure times to induce pyridinium-type crosslinks. These crosslinks are relevant to this model system as their centerpiece is the pyridine ring, which is also the central chemical feature of hydroxylysyl pyridinoline. Hydroxylysyl pyridinoline is a crosslink found in the extracellular matrix of articular cartilage, and its degradation is associated with loss of cartilage structural stability.

Clinical Model (Cartilage Explant Model)

In this model, β-aminopropionitrile (BAPN) was used as inhibitor blocking formation of pyridinoline (PYD) CxLs in an immature bovine articular cartilage explant model. In a cartilage explant model, levels of glucose, cortisol and insulin were controlled in a serum-free, chemically defined media to investigate the evolution of biochemical and mechanical properties of live immature bovine cartilage. It was determined that the presence of BAPN and the absence of cortisol each reduced PYD concentration, corresponding to loss of structural integrity of the cartilage.

72 samples were obtained from 4 joints divided into 4 groups, n=20 per group (n=5 from each joint) for +BAPN, −BAPN and −cortisol groups, n=12 for day 0 group.

For Raman characterization, n=16 were tested for +BAPN, −BAPN and −cortisol groups, and n=9 were tested for day 0 group on day 14. For each sample, 3 different spots were characterized. Therefore, 48 spectra were characterized for +BAPN, −BAPN and −cortisol groups and 27 spectra were characterized for the day 0 group.

Figure 8A:
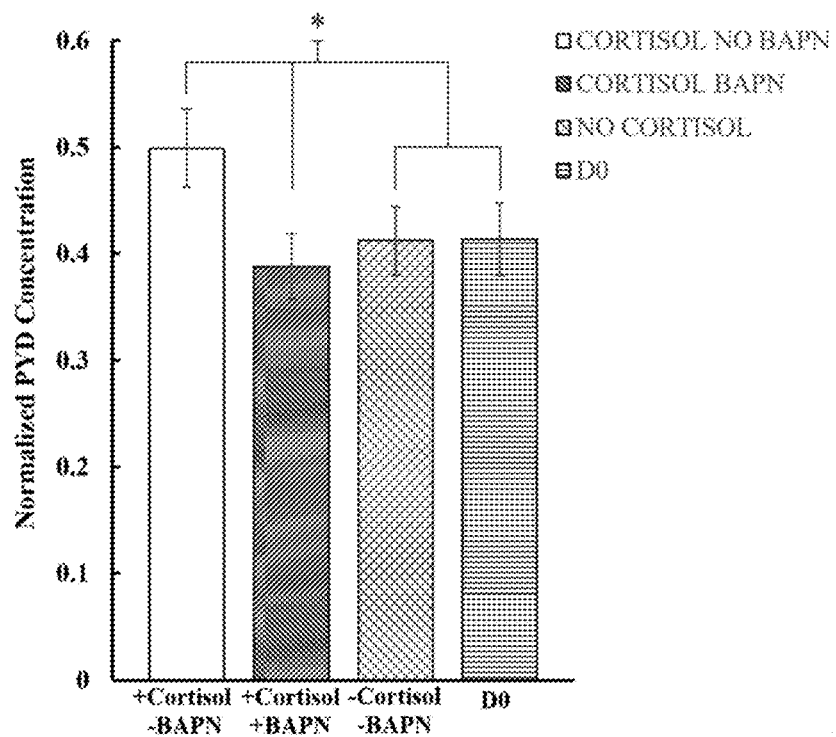
FIG. 8A shows pyridinoline collagen cross-links density measured at 1030 $cm^{-1}$ Raman band at D14 (+cortisol −β-aminopropionitrile, +cortisol +β-aminopropionitrile, −cortisol −β-aminopropionitrile, n=16 per group and 3 different locations were tested on each sample) and D0 (n=9 and 3 different locations were tested on each sample). Spectrum was normalized to proline peak at 857 $cm^{-1}$. A lower pyridinoline collagen cross-links concentration for +cortisol, +inhibitor group compared with +cortisol, −inhibitor group. Error bar: standard deviation. *p<0.01: statistical change of pyridinoline densities.
Figure 8B:
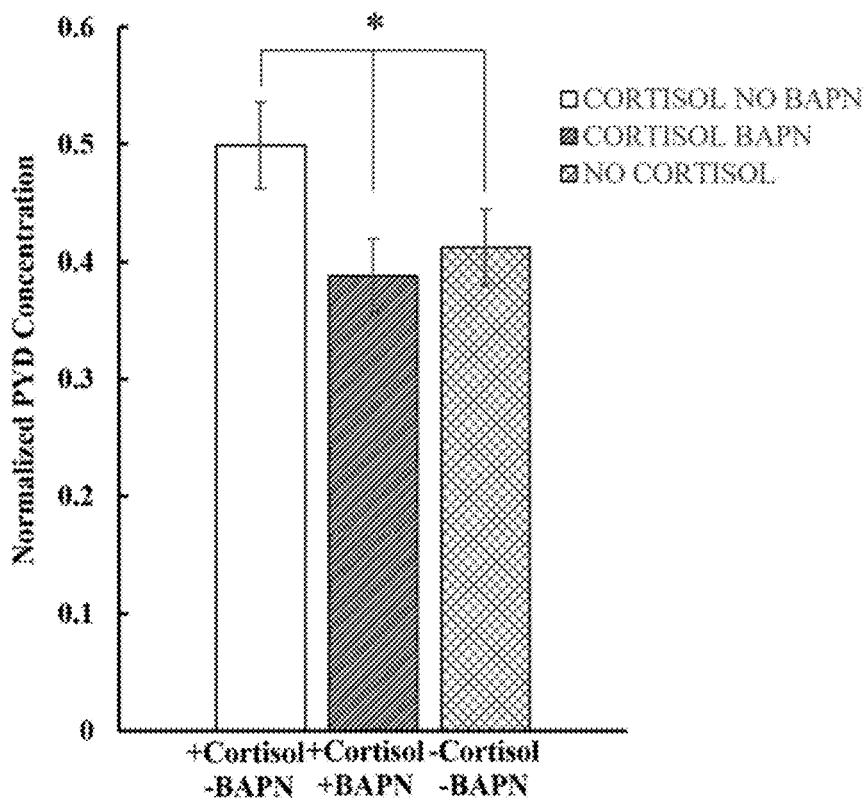
FIG. 8B shows pyridinoline collagen cross-links density measured at 1030 $cm^{-1}$ Raman band at D14 (n=16 per group and 3 different locations were tested on each sample). Spectrum was normalized to proline peak at 857 $cm^{-1}$. A lower pyridinoline collagen cross-links concentration for +cortisol, +inhibitor group compared with +cortisol, −inhibitor group. Error bar: standard deviation. *p<0.01: statistical change of pyridinoline densities.

Results are shown in FIGS. 8A and 8B. FIGS. 8A and 8B both show lower PYD CxLs concentration for +cortisol, +inhibitor group compared with +cortisol, −inhibitor group (the error bar shows standard deviation; *p<0.01: statistical change of PYD densities).

FIG. 8A shows PYD CxLs density measured at 1030 $cm^{-1}$ Raman band at D14 (+cortisol −BAPN, +cortisol +BAPN, −cortisol −BAPN, n=16 per group and 3 different locations were tested on each sample) and D0 (n=9 and 3 different locations were tested on each sample). The spectrum was normalized to proline peak at 857 $cm^{-1}$. A lower PYD CxLs concentration for +cortisol, +inhibitor group compared with +cortisol, −inhibitor group. FIG. 8B shows PYD CxLs density measured at 1030 cm-1 Raman band at D14 (n=16 per group and 3 different locations were tested on each sample). The spectrum was normalized to proline peak at 857 cm-1. Lower PYD CxLs concentration was found for +cortisol, +inhibitor group compared with +cortisol, −inhibitor group.

According to embodiments, the disclosed subject matter includes a method of analyzing mammal cartilage tissue. The method includes generating a Raman spectrum of cartilage tissue. The method further includes measuring one or more Raman spectrum peaks corresponding to a cartilage crosslinking moiety.

In embodiments, the cartilage may be articular cartilage. The articular cartilage may include collagen type I or collagen type II. The cartilage tissue may be of a patient with early stage osteoarthritis. The Raman spectrum may be generated using Raman micro-spectroscopy, selective-sampling Raman micro-spectroscopy, coherent anti-Stokes Raman spectroscopy (CARS), stimulated Raman spectroscopy (SRS), surface enhanced Raman spectroscopy (SERS), spatially offset Raman spectroscopy (SORS), surface enhanced spatially offset Raman spectroscopy (SESORS), or transmission Raman spectroscopy (TRS). The Raman spectrum may be generated in vivo. The Raman spectrum may be generated by endoscopy or arthoscopy. The Raman spectrum may be generated using an arthroscope. The Raman spectrum may be generated using a fiber optic Raman probe. The fiber optic Raman probe may be a handheld probe. The crosslinking moiety may contain a pyridinium ring or pentosidine. The crosslinking moiety may be hydroxylsylylpyridinoline.

According to further embodiments, the disclosed subject matter includes a method of analyzing Raman spectral data from collagen. The method includes decomposing a Raman signal from the collagen into predetermined chemical structures and their respective allowable vibrational modes. The method further includes modeling each of said predetermined chemical structures as a mathematical function. The method further includes combining the mathematical functions into an optimization function that produces a model of the spectra. The method further includes extracting information from the model indicative of changes in relative concentration of CxLs and quantitatively assessing changes in relative concentration of CxLs induced by glutaraldehyde fixation to diagnose the osteoarthritis.

In further variations of the foregoing method, the collagen is obtained from articular cartilage. In further embodiments of the foregoing method, the Raman spectral data is obtained using a confocal micro-spectrometer. In further embodiments of the foregoing method, the combining step includes curve fitting to produce the model of the spectra. In further embodiments of the foregoing method, the combining step includes iteratively fitting a fifth order polynomial and subtracting the fifth order polynomial from a raw signal of fluorescence.

According to still further embodiments, the disclosed subject matter includes a method of diagnosing osteoarthritis. The method includes decomposing a Raman signal from collagen into predetermined chemical structures and their respective allowable vibrational modes. The method further includes modeling each of said predetermined chemical structures as a mathematical function. The method further includes combining the mathematical functions into an optimization function that produces a model of the spectra. The method further includes extracting information from the model indicative of changes in relative concentration of CxLs. The method further includes quantitatively assessing changes in relative concentration of CxLs induced by glutaraldehyde fixation to diagnose the osteoarthritis.

In further variations of the foregoing methods, methods may include applying the Raman signal to cartilage in a joint or acquiring Raman spectra with a confocal micro-spectrometer.

The combining may include curve-fitting to produce the model of the spectra. The combining may include iteratively fitting a fifth order polynomial and subtracting the fifth order polynomial from a raw signal of fluorescence.

According to further embodiments, the disclosed subject matter includes a method of diagnosing osteoarthritis. The method may include scanning a cartilage at multiple locations of the cartilage to obtain Raman signal from each of the locations. The method may further include quantifying cross-linking in the cartilage responsively to said signal for each location. The method may further include generating a display of spatially-resolved magnitudes of cross-linking responsively to said quantifying.

The quantifying may include detecting magnitudes of peaks of a spectrum for each of said locations. The method may include classifying said cartilage according to a degree of osteoarthritis.

According to further embodiments, the disclosed subject matter includes a system for diagnosing osteoarthritis. An optical probe is configured to deliver excitation light and receive signal light responsively to Raman scattering resulting from illumination by said excitation light. A spectral analyzer is connected to the probe to receive said signal light and to generate reduced spectral data from a spectrum thereof. A machine classifier is programmed to distinguish between healthy and arthritic cartilage from said reduced spectral data and to output an indication responsive to a detected class.

The reduced spectral data may include a magnitude of at least one spectral peak. The reduced spectral data may include a magnitude of multiple spectral peaks. The reduced spectral data may include a magnitude of at least one spectral peak at each of multiple locations within a target sample.

The foregoing descriptions apply, in some cases, to examples generated in a laboratory, but these examples can be extended to production techniques. For example, where quantities and techniques apply to the laboratory examples, they should not be understood as limiting.

Features of the disclosed embodiments may be combined, rearranged, omitted, etc., within the scope of the invention to produce additional embodiments. Furthermore, certain features may sometimes be used to advantage without a corresponding use of other features.

It is, thus, apparent that there is provided, in accordance with the present disclosure, devices methods and systems for detecting features of collagen containing tissues and by way of example, particularly, for diagnosing osteoarthritis. Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicants intend to embrace all such alternatives, modifications, equivalents, and variations that are within the spirit and scope of the present invention.

It will be appreciated that the modules, processes, systems, and sections described above can be implemented in hardware, hardware programmed by software, software instruction stored on a non-transitory computer readable medium or a combination of the above. For example, a method for classifying Rama spectral data can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their subcomponents or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of machine classification and signal analysis and/or computer programming arts.

Moreover, embodiments of the disclosed method, system, and computer program product can be implemented in software executed on a programmed general purpose computer, a special purpose computer, a microprocessor, or the like.

The presently disclosed subject matter is not intended to be limited to the specific embodiments disclosed above. Although the foregoing subject matter has been described in some detail by way of illustration and example for purposes of clarity of understanding, the description above is not meant to be limiting, and those skilled in the art will understand that certain changes and modifications can be practiced within the scope of the claims. Thus, modifications and other embodiments are intended to be included within the scope of the appended claims.

The invention claimed is:

1. A method of analyzing mammal cartilage tissue, comprising:
    generating a Raman spectrum of cartilage tissue; and
    measuring one or more Raman spectrum peaks corresponding to a cartilage crosslinking moiety.

2. The method of claim 1, wherein the cartilage is articular cartilage.

3. The method of claim 2, wherein the articular cartilage comprises collagen type I or collagen type II.

4. The method of claim 1, wherein the cartilage tissue is of a patient with early stage osteoarthritis.

5. The method of claim 1, wherein the Raman spectrum is generated using Raman micro-spectroscopy, selective-sampling Raman micro-spectroscopy, coherent anti-Stokes Raman spectroscopy (CARS), stimulated Raman spectroscopy (SRS), surface enhanced Raman spectroscopy (SERS), spatially offset Raman spectroscopy (SORS), surface enhanced spatially offset Raman spectroscopy (SESORS), or transmission Raman spectroscopy (TRS).

6. The method of claim 1, wherein the Raman spectrum is generated in vivo.

7. The method of claim 6, wherein the Raman spectrum is generated by endoscopy or arthroscopy.

8. The method of claim 7, wherein the Raman spectrum is generated using an arthroscope.

9. The method of claim 8, wherein the Raman spectrum is generated using a fiber optic Raman probe.

10. The method of claim 9, wherein the fiber optic Raman probe is a handheld probe.

11. The method of claim 1, wherein the crosslinking moiety contains a pyridinium ring or pentosidine.

12. The method of claim 1, wherein the crosslinking moiety is hydroxylsylylpyridinoline.

13. A method of analyzing Raman spectral data from collagen, comprising:
   decomposing a Raman signal from the collagen into predetermined chemical structures and their respective allowable vibrational modes;
   modeling each of said predetermined chemical structures as a mathematical function;
   combining the mathematical functions into an optimization function that produces a model of the spectra;
   extracting information from the model indicative of changes in relative concentration of CxLs; and
   quantitatively assessing changes in relative concentration of CxLs induced by glutaraldehyde fixation to diagnose the osteoarthritis.

14. The method of claim 13, wherein the collagen is obtained from articular cartilage.

15. The method of claim 14, wherein the Raman spectral data is obtained using a confocal micro-spectrometer.

16. The method of claim 13, wherein the combining step includes curve fitting to produce the model of the spectra.

17. The method of claim 13, wherein the combining step includes iteratively fitting a fifth order polynomial and subtracting the fifth order polynomial from a raw signal of fluorescence.

18. A method of diagnosing osteoarthritis, the method comprising:
   decomposing a Raman signal from collagen into predetermined chemical structures and their respective allowable vibrational modes;
   modeling each of said predetermined chemical structures as a mathematical function;
   combining the mathematical functions into an optimization function that produces a model of the spectra;
   extracting information from the model indicative of changes in relative concentration of CxLs; and
   quantitatively assessing changes in relative concentration of CxLs induced by glutaraldehyde fixation to diagnose the osteoarthritis.

19. The method according to claim 18, further comprising:
   applying the Raman signal to cartilage in a joint.

20. The method according to claim 19, further comprising:
   acquiring Raman spectra with a confocal micro-spectrometer.

21. The method according to claim 18, wherein
   the combining step includes curve fitting to produce the model of the spectra.

22. The method according to claim 21, wherein the combining includes
   iteratively fitting a fifth order polynomial and subtracting the fifth order polynomial from a raw signal of fluorescence.

* * * * *